US008153839B2

(12) United States Patent
Ogo et al.

(10) Patent No.: US 8,153,839 B2
(45) Date of Patent: Apr. 10, 2012

(54) METHOD FOR SYNTHESIS OF KETO ACIDS OR AMINO ACIDS BY HYDRATION OF ACETYLENE COMPOUND

(75) Inventors: Seiji Ogo, Fukuoka (JP); Shun-ichi Fukuzumi, Osaka (JP)

(73) Assignee: Japan Science and Technology Agency, Kawaguchi-shi (JP)

( * ) Notice: Subject to any disclaimer, the term of this patent is extended or adjusted under 35 U.S.C. 154(b) by 579 days.

(21) Appl. No.: 12/066,491

(22) PCT Filed: Sep. 13, 2006

(86) PCT No.: PCT/JP2006/318199
§ 371 (c)(1),
(2), (4) Date: May 14, 2009

(87) PCT Pub. No.: WO2007/032409
PCT Pub. Date: Mar. 22, 2007

(65) Prior Publication Data
US 2009/0216044 A1 Aug. 27, 2009

(30) Foreign Application Priority Data
Sep. 14, 2005 (JP) ................................ 2005-267461

(51) Int. Cl.
C07C 61/00 (2006.01)
C07C 205/00 (2006.01)
(52) U.S. Cl. ........................................ 562/400; 562/553
(58) Field of Classification Search .................. 562/400, 562/553
See application file for complete search history.

(56) References Cited

FOREIGN PATENT DOCUMENTS
WO 2005/028419 A2 3/2005

OTHER PUBLICATIONS

Office Action for Japanese Patent Application No. 2007-535523, mailed on Jan. 25, 2011, 5 pages (3 pages of English Translation and 2 pages of Office Action).
Ogo et al., "pH-Selective Synthesis and Structures of Alkynyl, Acyl, and Ketonyl Intermediates in Anti-Markovnikov and Markovnikov Hydrations of a Terminal Alkyne with a Water-Soluble Iridium Aqua Complex in Water", Journal of American Chemical Society, vol. 126, 2004, pp. 16520-16527.
Bassetti, M. et al. (1989). "Metalation of Alkynes. 4. The Methoxymercuration Reaction," *Journal of Organic Chemistry* 54(25):5934-5938.
Tani, K. et al. (1998). "Reductive Dimerization of Dialkyl Acetylenedicarboxylate Catalyzed by [Rh(binap)(MeOH$_2$)]ClO$_4$ in Methanol," *Journal of Organometallic Chemistry* 560(1-2):253-255.
International Search Report mailed on Dec. 12, 2006, for PCT Application No. PCT/JP2006/318199 filed on Sep. 13, 2006, 7 pages.
Extended European Search Report for European Patent Application No. 06797949.2, mailed on Sep. 30, 2011, 8 pages.
Menashe et al., "Hydration of Alkynes in Anhydrous Medium with Formic Acid as Water Donor", J. Org. Chem., vol. 58, No. 26, 1993, pp. 7434-7439.
Beller, M. et al. (2004). "Catalytic Markovnikov and Anti-Markivnikov Functionalization of Alkenes and Alkynes: Recent Developments and Trends," *Angewandte Chemie International Edition* 43:3368-3398.
Larock, R. C. et al. (1991). "Addition of H-X Reagents to Alkenes and Alkynes" Chapter 1.7 in *Comprehensive Organize Synthesis: Selectivity, Strategy & Efficiency in Modern Organic Chemistry*, vol. 4 Additions to and Substitutions at C—C π-Bonds. B. M. Trost et al. eds., Pergamon Press, pp. 269-327.
March, J. (1992). "5-3 Hydration of Triple Bonds"in *Advanced Organic Chemistry: Reactions, Mechanisms and Structure*. 4th Edition, John Wiley & Sons, pp. 762-763.

*Primary Examiner* — Jafar Parsa
(74) *Attorney, Agent, or Firm* — Morrison & Foerster LLP

(57) ABSTRACT

An object of the present invention is to provide a method for synthesis of keto acids by hydration of an acetylene compound (acetylene-carboxylic acids) under mild conditions free from harmful mercury catalysts and a method for synthesis of amino acids from acetylene-carboxylic acids in a single container (one-pot or tandem synthesis). In one embodiment of the method according to the present invention for synthesis of keto acids, acetylene-carboxylic acids is hydrated in the presence of a metal salt represented by General Formula (1), General Formula (1)

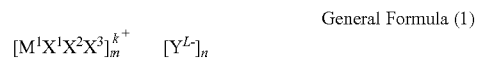

where $M^1$ represents an element in Group VIII, IX, or X of the periodic table, and $X^1$, $X^2$, or $X^3$ ligand represents halogen, $H_2O$, or a solvent molecule, and k represents a valence of a cation species, and Y represents an anion species, and L represents a valence of the anion species, and each of K and L independently represents 1 or 2, and k×m=L×n.

6 Claims, 3 Drawing Sheets

Path A

Acetylene-carboxylic acids                     $\alpha$-keto acids

Path C

Acetylene-carboxylic acids                     $\beta$-keto acids

Path B

Path D

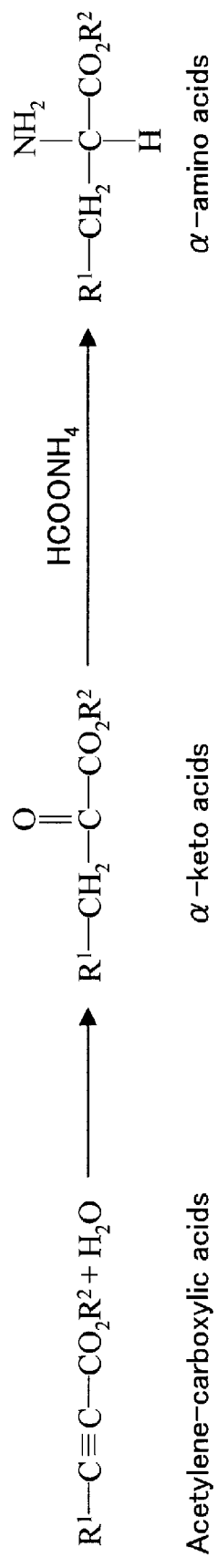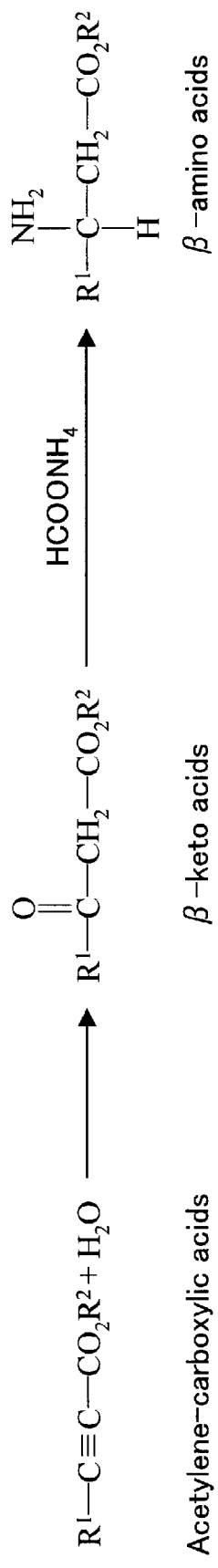
F I G. 3 (a) Path A+B
F I G. 3 (b) Path C+D

METHOD FOR SYNTHESIS OF KETO ACIDS OR AMINO ACIDS BY HYDRATION OF ACETYLENE COMPOUND

CROSS REFERENCE TO RELATED APPLICATIONS

This application is a U.S. National Phase application of PCT/JP2006/318199 filed Sep. 13, 2006, which claims priority to Japan Patent Application Serial No. 2005-267461 filed Sep. 14, 2005, the contents of which are hereby incorporated by reference in the present disclosure in their entirety.

TECHNICAL FIELD

The present invention relates to a method for synthesis of keto acids (including keto acid and keto acid derivative) by hydration of acetylene-carboxylic acids in the presence of a transition metal salt or a transition metal complex.

Further, the present invention relates to a method for synthesis of amino acids (including amino acid and amino acid derivative) from acetylene-carboxylic acids in a single container (one-pot or tandem synthesis) by sequentially performing hydration of acetylene-carboxylic acids and reductive amination of keto acids (including keto acid and keto acid derivative).

BACKGROUND ART

There are many studies on hydration of acetylene compound (e.g., Non-Patent Documents 1 to 3). However, the hydration is performed in the presence of mercury catalysts, which are harmful for humans and environment. It has not been reported that keto acids and keto acid derivatives (keto esters and the like) are synthesized from acetylene compound.

[Non-Patent Document 1]
R. C. Larock et al. "In Comprehensive Organic Synthesis" Ed. 1991, 4.269

[Non-Patent Document 2]
J. March. "Advanced Organic Chemistry", 1992, 762

[Non-Patent Document 3]
M. Beller et al. Angew. Chem., Int. Ed. 2004 43, 3368

The object of the present invention is to provide a method for synthesis of keto acids (including keto acid and keto acid derivative) by hydration of acetylene-carboxylic acids under mild conditions free from any harmful mercury catalysts. Further, the object of the present invention is to provide a method for synthesis of amino acids (including amino acid and amino acid derivative) from acetylene-carboxylic acids in a single container (one-pot or tandem synthesis) by sequentially performing hydration of acetylene-carboxylic acids and reductive amination of keto acids (including keto acid and keto acid derivative).

DISCLOSURE OF INVENTION

The inventors of the present invention diligently studied to solve the foregoing problems. As a result, they completed the present invention.

That is, in order to solve the foregoing problems, the following inventions are adopted.

(a) A method for synthesis of keto acids, comprising the step of hydrating acetylene-carboxylic acid in the presence of at least one selected from a group consisting of a metal salt represented by General Formula (1), a transition metal complex represented by General Formula (2), a transition metal complex represented by General Formula (3), and a transition metal complex represented by General Formula (8), General Formula (1)

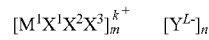

where $M^1$ represents an element in Group VIII, IX, or X of the periodic table, and $X^1$, $X^2$, or $X^3$ ligand represents halogen, $H_2O$, or a solvent molecule, and k represents a valence of a cation species, and Y represents an anion species, and L represents a valence of the anion species, and each of K and L independently represents 1 or 2, and k×m=L×n, General Formula (2)

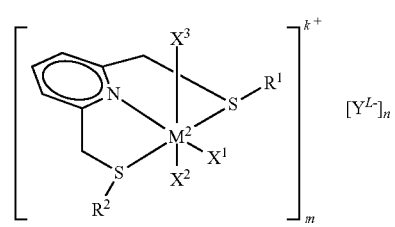

where each of $R^1$ and $R^2$ independently represents a hydrogen atom or a lower alkyl group, and $M^2$ represents an element in Group VIII, IX, or XI of the periodic table, and $X^1$ or $X^2$ ligand represents $H_2O$, halogen, a solvent molecule, or nitrous ligand, and $X^3$ ligand represents halogen, $H_2O$, or a solvent molecule, and k represents a valence of a cation species, and Y represents an anion species, and L represents a valence of the anion species, and each of K and L independently represents 1 or 2, and k×m=L×n, General Formula (3)

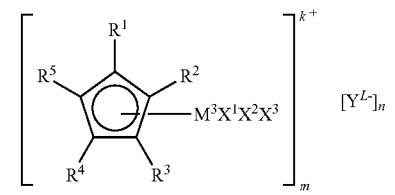

where each of $R^1$, $R^2$, $R^3$, $R^4$, and $R^5$ independently represents a hydrogen atom or a lower alkyl group, and $M^3$ represents an element in Group VIII or IX of the periodic table, and each of $X^1$ and $X^2$ represents nitrous ligand, and $X^3$ represents a hydrogen atom, a carboxylic acid residue, or $H_2O$, and $X^1$ and $X^2$ may be bonded to each other, and k represents a valence of a cation species, and Y represents an anion species, and L represents a valence of the anion species, and each of K and L independently represents 1 or 2, and k×m=L×n, General Formula (8)

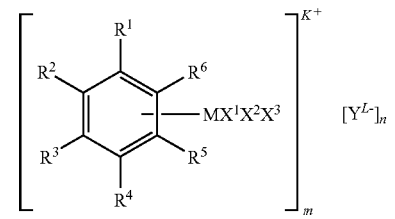

where each of $R^1$, $R^2$, $R^3$, $R^4$, $R^5$ and $R^6$ independently represents a hydrogen atom or a lower alkyl group, and M represents an element in Group VIII of the periodic table, and each of $X^1$, $X^2$ and $X^3$ represents halogen, $H_2O$, or a solvent molecule, and k represents a valence of a cation species, and Y represents an anion species, and L represents a valence of the anion species, and each of K and L independently represents 1 or 2, and k×m=L×n.

(b) The method as set forth in claim 1, wherein the metal salt is such that $M^1$ is Ru, Rh, or Ir in General Formula (1).

(c) The method based on the method (a), wherein the transition metal complex is such that $M^2$ is Ru or Rh in General Formula (2).

(d) The method based on any one of the methods (a) to (c), wherein the hydration is performed in the presence of an organic solvent which is inert in reaction.

(e) A method for synthesis of amino acids, comprising the steps of:

hydrating acetylene-carboxylic acid in the presence of a metal salt represented by General Formula (1); and adding a transition metal complex represented by General Formula (3) and a hydrogen and nitrogen atom donor to a reaction system of the hydrated acetylene-carboxylic acids so as to cause a reaction thereof, General Formula (1)

where $M^1$ represents an element in Group VIII, IX, or X of the periodic table, and $X^1$, $X^2$, or $X^3$ ligand represents halogen, $H_2O$, or a solvent molecule, and k represents a valence of a cation species, and Y represents an anion species, and L represents a valence of the anion species, and each of K and L independently represents 1 or 2, and k×m=L×n, General Formula (3)

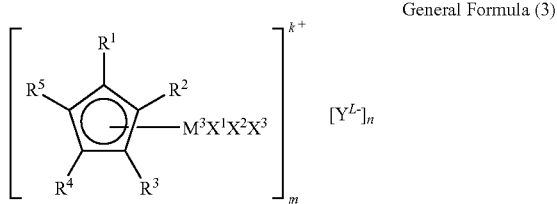

where each of $R^1$, $R^2$, $R^3$, $R^4$, and $R^5$ independently represents a hydrogen atom or a lower alkyl group, and $M^3$ represents an element in Group VIII or IX of the periodic table, and each of $X^1$ and $X^2$ represents nitrous ligand, and $X^3$ represents a hydrogen atom, a carboxylic acid residue, or $H_2O$ and $X^1$ and $X^2$ may be bonded to each other, and k represents a valence of a cation species, and Y represents an anion species, and L represents a valence of the anion species, and each of K and L independently represents 1 or 2, and k×m=L×n.

(f) A method for synthesis of amino acids, comprising the steps of:

hydrating acetylene-carboxylics acid in the presence of a transition metal complex represented by General Formula (2); and adding a transition metal complex represented by General Formula (3) and a nitrogen atom donor to a reaction system of the hydrated acetylene-carboxylic acids so as to cause a reaction thereof, General Formula (2)

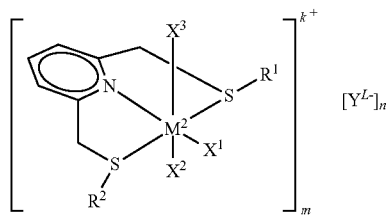

where each of $R^1$ and $R^2$ independently represents a hydrogen atom or a lower alkyl group, and $M^2$ represents an element in Group VIII, IX, or X of the periodic table, and $X^1$ or $X^2$ ligand represents $H_2O$, halogen, a solvent molecule, or nitrous ligand, and $X^3$ ligand represents halogen, $H_2O$, or a solvent molecule, and k represents a valence of a cation species, and Y represents an anion species, and L represents a valence of the anion species, and each of K and L independently represents 1 or 2, and k×m=L×n, General Formula (3)

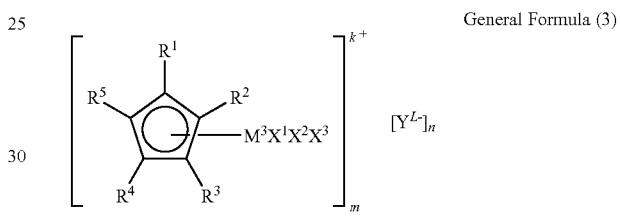

where each of $R^1$, $R^2$, $R^3$, $R^4$, and $R^5$ independently represents a hydrogen atom or a lower alkyl group, and $M^3$ represents an element in Group VIII or IX of the periodic table, and each of $X^1$ and $X^2$ represents nitrous ligand, and $X^3$ represents a hydrogen atom, a carboxylic acid residue, or $H_2O$, and $X^1$ and $X^2$ may be bonded to each other, and k represents a valence of a cation species, and Y represents an anion species, and L represents a valence of the anion species, and each of K and L independently represents 1 or 2, and k×m=L×n.

(g) A method for synthesis of amino acids, comprising the steps of:

hydrating acetylene-carboxylic acid in the presence of at least one selected from a group consisting of a transition metal complex represented by General Formula (2), a transition metal complex represented by General Formula (3), and a transition metal complex represented by General Formula (8); and adding a hydrogen and nitrogen atom donor to a reaction system of the hydrated acetylene-carboxylic acids so as to cause a reaction thereof, General Formula (2)

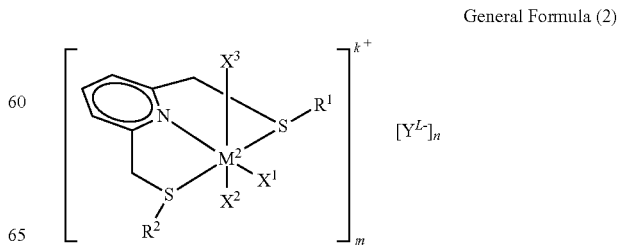

where each of $R^1$ and $R^2$ independently represents a hydrogen atom or a lower alkyl group, and $M^2$ represents an element in Group VIII, IX, or X of the periodic table, and $X^1$, or $X^2$ ligand represents $H_2O$, halogen, a solvent molecule, or nitrous ligand, and $X^3$ ligand represents halogen, $H_2O$, or a solvent molecule, and k represents a valence of a cation species, and Y represents an anion species, and L represents a valence of the anion species, and each of K and L independently represents 1 or 2, and k×m=L×n, General Formula (3)

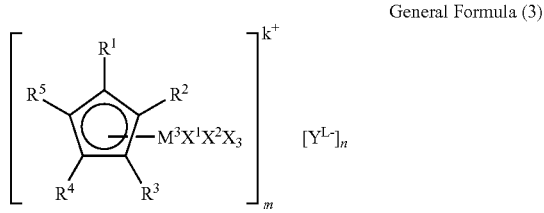

where each of $R^1$, $R^2$, $R^3$, $R^4$, and $R^5$ independently represents a hydrogen atom or a lower alkyl group, and $M^3$ represents an element in Group VIII or IX of the periodic table, and each of $X^1$ and $X^2$ represents nitrous ligand, and $X^3$ represents a hydrogen atom, a carboxylic acid residue, or $H_2O$, and $X^1$ and $X^2$ may be bonded to each other, and k represents a valence of a cation species, and Y represents an anion species, and L represents a valence of the anion species, and each of K and L independently represents 1 or 2, and k×m=L×n, General Formula (8)

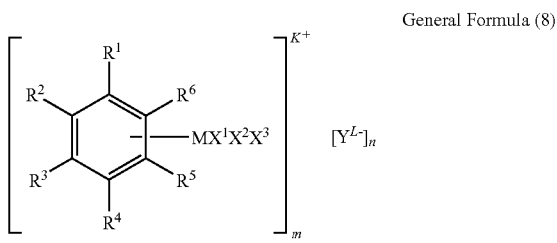

where each of $R^1$, $R^2$, $R^3$, $R^4$, $R^5$ and $R^6$ independently represents a hydrogen atom or a lower alkyl group, and M represents an element in Group VIII of the periodic table, and each of $X^1$, $X^2$ and $X^3$ represents halogen, $H_2O$, or a solvent molecule, and k represents a valence of a cation species, and Y represents an anion species, and L represents a valence of the anion species, and each of K and L independently represents 1 or 2, and k×m=L×n.

(h) A method for synthesis of amino acids, comprising the steps of:
hydrating acetylene-carboxylic acid in the presence of a metal salt represented by General Formula (1); and
adding organic ligand respectively represented by General Formula (4) and General Formula (5) and a hydrogen and nitrogen atom donor to a reaction system of the hydrated acetylene-carboxylic acids so as to cause a reaction thereof, General Formula (1)

where $M^1$ represents an element in Group VIII, IX, or X of the periodic table, and $X^1$, $X^2$, or $X^3$ ligand represents halogen, $H_2O$, or a solvent molecule, and k represents a valence of a cation species, and Y represents an anion species, and L represents a valence of the anion species, and each of K and L independently represents 1 or 2, and k×m=L×n, General Formula (4)

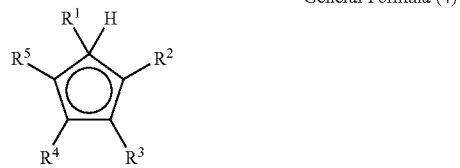

where each of $R^1$, $R^2$, $R^3$, $R^4$, and $R^5$ independently represents a hydrogen atom or a lower alkyl group, General Formula (5)

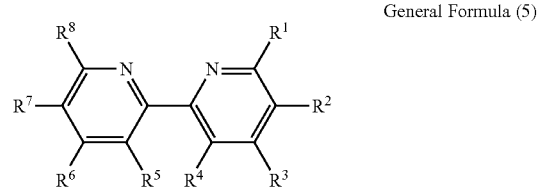

where each of $R^1$, $R^2$, $R^3$, $R^4$, $R^5$, $R^6$, $R^7$, and $R^8$ independently represents a hydrogen atom or a lower alkyl group The hydration of the present invention with use of a metal salt and a transition metal complex allows synthesis of keto acids (including keto acid and keto acid derivative) from acetylene-carboxylic acids under mild conditions without using extremely harmful mercury catalysts. The hydration is extremely useful as environmental friendly conversion. Moreover, according to the present invention, it is possible to easily synthesize amino acids (including amino acid and amino acid derivative) from the synthesized keto acids (including keto acid and keto acid derivative) by subsequent reductive amination in the same container. Also in view of creation of a new technology, it is infinitely valuable to easily synthesize amino acids (including amino acid and amino acid derivative) which are extremely significant in medical and biochemistry fields.

Further, the synthesis of amino acids (including amino acid and amino acid derivative) from acetylene-carboxylic acids means also synthesis of amino acids (including amino acid and amino acid derivative) with use of coal as a raw material. Currently, oil is used as a raw material to synthesize amino acids (including amino acid and amino acid derivative). According to the present invention, it is possible to realize such effect that amino acids (including amino acid and amino acid derivative) can be synthesized without using oil resources whose depletion is serious concern.

For a fuller understanding of the nature and advantages of the invention, reference should be made to the ensuing detailed description taken in conjunction with the accompanying drawings.

BRIEF DESCRIPTION OF DRAWINGS

FIG. 3(a) is a drawing illustrating a reaction formula of one-pot synthesis of amino acids (including amino acid and amino acid derivative) from acetylene-carboxylic acids with use of acetylene-carboxylic acids as starting material in Examples.

FIG. 3(b) is a drawing illustrating a reaction formula of one-pot synthesis of amino acids (including amino acid and amino acid derivative) from acetylene-carboxylic acids with use of acetylene-carboxylic acids as starting material in Examples.

BEST MODE FOR CARRYING OUT THE INVENTION

Figure 1:
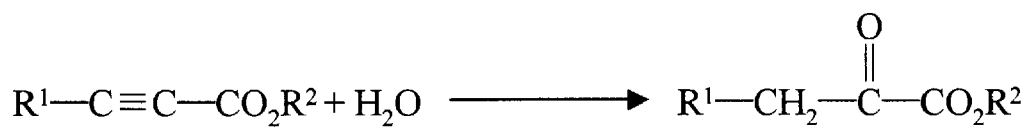
FIG. 1(a) is a drawing illustrating a reaction formula of synthesis of α-keto acids (including α-keto acid and α-keto acid derivative) by hydration of acetylene-carboxylic acids in the presence of various kinds of metal salts or transmission metal complexes.
FIG. 1(b) is a drawing illustrating a reaction formula of synthesis of β-keto acids (including β-keto acid and β-keto acid derivative) by hydration of acetylene-carboxylic acids in the presence of various kinds of metal salts or transmission metal complexes in Examples and Comparative Examples.
Figure 1:
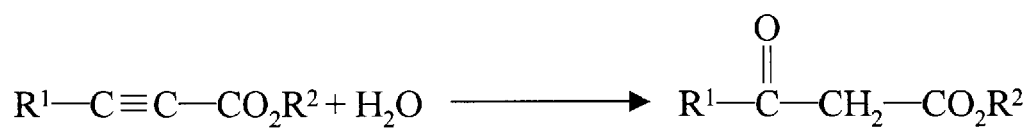

The following explains an embodiment of the present invention. Note that, the present invention is not limited to this.

First, a metal salt (transition metal salt) and a transition metal complex that are used in the present invention are explained as follows.

<Metal Salt Represented by General Formula (1)>

In the metal salt represented by General Formula (1), $M^1$ is not particularly limited as long as $M^1$ is a transition metal element in Group VIII, IX, or X of the periodic table, but it is preferable to use, as the transition metal element, ruthenium (hereinafter, referred to as "Ru" as necessary), rhodium (hereinafter, referred to as "Rh" as necessary), iridium (hereinafter, referred to as "Ir" as necessary), and the like.

Further, examples of $X^1$, $X^2$, or $X^3$ ligand include $H_2O$, halogen, and the like. Also a solvent molecule serves as the ligand. Examples of the solvent molecule include methanol, ethanol, acetonitrile, tetrahydrofuran, pyridine, dimethylsulfoxide, dimethylformamide, and the like.

Examples of an anion species represented by Y include carboxylic acid ion such as formic acid and acetic acid, sulfate ion, fluoride ion, chloride ion, bromide ion, iodide ion, triflurt ion, perchloriante ion, perbromate ion, periodate ion, tetrafluoro borate ion, hexafluoro phosphate ion, thiocyanate ion, and the like.

Specific examples of the metal salt represented by General Formula (1) include ruthenium trichloride, rhodium trichloride, and iridium trichloride. The metal salt may be an anhydride or a hydrate (e.g., trihydrate or the like). A commercially available metal salt is used as the aforementioned metal salt. For example, ruthenium trichloride and iridium trichloride are available from Tanaka Metal Co., Ltd. and rhodium trichloride is available from Furuya Metal Co., Ltd.

<Transition Metal Complex Represented by General Formula (2)>

In the transition metal complex represented by General Formula (2), each of $R^1$ and $R^2$ independently represents a hydrogen atom or a lower alkyl group. Examples of the lower alkyl group include an alkyl group whose carbon number is 1-6, specifically, a methyl group, an ethyl group, a propyl group, a butyl group, a pentyl group, a hexyl group, an isopropyl group, a t-butyl group, an isoamyl group, a cyclopentyl group, a cyclohexyl group, and the like.

Further, in the transition metal complex, $M^2$ is not particularly limited as long as $M^2$ is a transition metal element in Group VIII, IX, or X of the periodic table, but it is preferable to use Ru, Rh, Pd (palladium), and the like.

Further, examples of $X^1$ or $X^2$ ligand include $H_2O$, halogen, a solvent molecule, nitrous ligand, and the like. Examples of the "nitrous ligand" include pyrrole, pyridine, imidazole, N-methylimidazole, acetonitrile, ammonia, aniline, 1,2-ethanediamine, 1,2-diphenyl-1,2-ethanediamine, 1,2-cyclohexadiamine, 2,2'-bipyridine, 1,10-phenanthroline, and the like. More preferred is bidentate ligand, still more preferred is 2,2'-bipyridine or a derivative thereof. Examples of the "solvent molecule" include methanol, ethanol, acetonitrile, tetrahydrofuran, pyridine, dimethylsulfoxide, dimethylformamide, and the like. Further, $X^3$ ligand is the same as in the "metal salt represented by General Formula (1)".

Also "Y" is the same as in the "metal salt represented by General Formula (1)".

Specific examples of the transition metal complex represented by General Formula (2) include di[triaqua {2,6-di(methylthiomethyl)pyridine} ruthenium (III)] 3-sulphate, di[triaqua {2,6-di(ethylthiomethyl)pyridine} ruthenium (III)] 3-sulphate, di[triaqua {2,6-di(isopropylthiomethyl)pyridine} ruthenium (III)] 3-sulphate, di[triaqua {2,6-di(t-butylthiomethyl)pyridine} ruthenium (III)] 3-sulphate, di[triaqua {2,6-di(phenylthiomethyl)pyridine} ruthenium (III)] 3-sulphate, triaqua[2,6-di(methylthiomethyl) pyridine] ruthenium (III)] 3-nitrate, triaqua[2,6-di(ethylthiomethyl) pyridine] ruthenium (III)] 3-nitrate, triaqua[2,6-di(isopropylthiomethyl)pyridine] ruthenium (III)] 3-nitrate, triaqua[2,6-di (t-butylthiomethyl)pyridine] ruthenium (III)] 3-nitrate, triaqua[2,6-di(phenylthiomethyl) pyridine] ruthenium (III)] 3-nitrate, triaqua[2,6-di(methylthiomethyl) pyridine] ruthenium (III)] 3-trifluoromethanesulfonate, triaqua[2,6-di(ethylthiomethyl)pyridine] ruthenium (III)] 3-trifluoromethanesulfonate, triaqua[2,6-di(isopropylthiomethyl)pyridine] ruthenium (III)] 3-trifluoromethanesulfonate, triaqua[2,6-di (t-butylthiomethyl)pyridine] ruthenium (III)] 3-trifluoromethanesulfonate, triaqua[2,6-di(phenylthiomethyl)pyridine] ruthenium (III)] 3-trifluoromethanesulfonate, triaqua [2,6-di(methylthiomethyl)pyridine] ruthenium (III)] 3-perchlorate, triaqua[2,6-di(ethylthiomethyl)pyridine] ruthenium (III)] 3-perchlorate, triaqua[2,6-di(isopropylthiomethyl)pyridine] ruthenium (III)] 3-perchlorate, triaqua[2,6-di(t-butylthiomethyl) pyridine] ruthenium (III)] 3-perchlorate, triaqua[2,6-di(phenylthiomethyl) pyridine] ruthenium (III)] 3-perchlorate, triaqua[2,6-di(methylthiomethyl)pyridine] ruthenium (III)] 3-tetrafluoroborate, triaqua[2,6-di(ethylthiomethyl) pyridine] ruthenium (III)] 3-tetrafluoroborate, triaqua[2,6-di(isopropylthiomethyl)pyridine] ruthenium (III)] 3-tetrafluoroborate, triaqua[2,6-di(t-butylthiomethyl) pyridine] ruthenium (III)] 3-tetrafluoroborate, triaqua[2,6-di (phenylthiomethyl) pyridine] ruthenium (III)] 3-tetrafluoroborate, di[triaqua {2,6-di(methylthiomethyl)pyridine} rhodium (III)] 3-sulphate, di[triaqua {2,6-di(ethylthiomethyl)pyridine} rhodium (III)] 3-sulphate, di[triaqua {2,6-di (isopropylthiomethyl) pyridine} rhodium (III)] 3-sulphate, di[triaqua {2,6-di(t-butylthiomethyl) pyridine} rhodium (III)] 3-sulphate, di[triaqua {2,6-di(phenylthiomethyl)pyridine} rhodium (III)] 3-sulphate, triaqua[2,6-di(methylthiomethyl) pyridine] rhodium (III)] 3-nitrate, triaqua[2,6-di(ethylthiomethyl)pyridine] rhodium (III)] 3-nitrate, triaqua[2,6-di(isopropylthiomethyl) pyridine] rhodium (III)] 3-nitrate, triaqua[2,6-di(t-butylthiomethyl)pyridine] rhodium (III)]

3-nitrate, triaqua[2,6-di(phenylthiomethyl)pyridine] rhodium (III)] 3-nitrate, triaqua[2,6-di(methylthiomethyl)pyridine] rhodium (III)] 3-trifluoromethanesulfonate, triaqua [2,6-di(ethylthiomethyl)pyridine] rhodium (III)] 3-trifluoromethanesulfonate, triaqua[2,6-di(isopropylthiomethyl)pyridine] rhodium (III)] 3-trifluoromethanesulfonate, triaqua[2,6-di(t-butylthiomethyl)pyridine] rhodium (III)] 3-trifluoromethanesulfonate, triaqua[2,6-di(phenylthiomethyl)pyridine] rhodium (III)] 3-trifluoromethanesulfonate, triaqua[2,6-di(methylthiomethyl)pyridine] rhodium (III)] 3-perchlorate, triaqua[2,6-di(ethylthiomethyl)pyridine] rhodium (III)] 3-perchlorate, triaqua[2,6-di(isopropylthiomethyl)pyridine] rhodium (III)] 3-perchlorate, triaqua[2,6-di(t-butylthiomethyl) pyridine] rhodium (III)] 3-perchlorate, triaqua[2,6-di(phenylthiomethyl)pyridine] rhodium (III)] 3-perchlorate, triaqua[2,6-di(methylthiomethyl) pyridine] rhodium (III)] 3-tetrafluoroborate, triaqua[2,6-di(ethylthiomethyl) pyridine] rhodium (III)] 3-tetrafluoroborate, triaqua [2,6-di(isopropylthiomethyl)pyridine] rhodium (III)] 3-tetrafluoroborate, triaqua[2,6-di(t-butylthiomethyl)pyridine] rhodium (III)] 3-tetrafluoroborate, triaqua[2,6-di(phenylthiomethyl) pyridine] rhodium (III)] 3-tetrafluoroborate, and the like.

The transition metal complex represented by General Formula (2) of the present invention can be produced in accordance with the following method for example. In the presence of water having a pH 3.8, trichloro[2,6-di(phenylthiomethyl)pyridine] ruthenium (III) is reacted with sulfate to give di[triaqua {2,6-di(phenylthiomethyl)pyridine} ruthenium (III)] 3-sulphate. A reaction temperature is generally from −40 to 200° C., but a preferred reaction temperature is −20 to 100° C. A reaction time varies depending on reaction conditions such as a reaction substrate concentration, a temperature, and the like, but the reaction is generally completed in several hours to 30 hours.

Note that, also a transition metal complex obtained by substituting "N" of the transition metal complex represented by General Formula (2) with "C" and a transition metal complex obtained by substituting "S" of the transition metal complex represented by General Formula (2) with "N" or "P" are applicable to the method of the present invention. Further, also a transition metal complex obtained by substituting "N" of the transition metal complex represented by General Formula (2) with "C" and substituting "S" of the transition metal complex with "N" or "P" is applicable to the method of the present invention.

<Transition Metal Complex Represented by General Formula (3)>

In a transition metal complex represented by General Formula (3), examples of $R^1$, $R^2$, $R^3$, $R^4$, or $R^5$ lower alkyl group include an alkyl group whose carbon number is 1-6, specifically, a methyl group, an ethyl group, a propyl group, a butyl group, a pentyl group, a hexyl group, an isopropyl group, a t-butyl group, an isoamyl group, a cyclopentyl group, a cyclohexyl group, and the like.

Further, in the transition metal complex represented by General Formula (3), any element may be used as $M^3$ element in Group VIII or IX of the periodic table as long as the element is capable of forming a Cp ring (cyclopentadienyl ring). Preferred elements are Rh, Ru, Ir, and the like.

Further, examples of nitrous ligand $X^1$ or $X^2$ in the transition metal complex represented by General Formula (3) include pyrrole, pyridine, imidazole, N-methylimidazole, acetonitrile, ammonia, aniline, 1,2-ethanediamine, 1,2-diphenyl-1,2-ethanediamine, 1,2-cyclohexadiamine, 2,2'-bipyridine, 1,10-phenanthroline, and the like. More preferred is bidentate ligand, still more preferred is 2,2'-bipyridine or a derivative thereof. Further, ligand $X^3$ in the transition metal complex represented by General Formula (3) is a hydrogen atom, a carboxylate residue, or $H_2O$. The "carboxylate residue" refers to a ligand having a carboxylic acid.

Examples of an anion species represented by Y include carboxylic acid ion such as formic acid and acetic acid, sulfate ion, fluoride ion, chloride ion, bromide ion, iodide ion, triflurt ion, perchloriante ion, perbromate ion, periodate ion, tetrafluoro borate ion, hexafluoro phosphate ion, thiocyanate ion, and the like.

Specific examples of the transition metal complex represented by General Formula (3) include triaqua[(1,2,3,4,5-η)-2,4-cyclopentadien-1-yl] cobalt (III) sulphate, triaqua[(1,2,3,4,5-η)-2,4-cyclopentadien-1-yl] rhodium (III) sulphate, triaqua[(1,2,3,4,5-η)-2,4-cyclopentadien-1-yl] iridium (III) sulphate, triaqua[(1,2,3,4,5-η)-1,2,3,4,5-pentamethyl-2,4-cyclopentadien-1-yl]cobalt (III) sulphate, triaqua[(1,2,3,4,5-η)-1,2,3,4,5-pentamethyl-2,4-cyclopentadien-1-yl] rhodium (III) sulphate, triaqua[(1,2,3,4,5-η)-1,2,3,4,5-pentamethyl-2,4-cyclopentadien-1-yl] iridium (III) sulphate, triaqua[(1,2,3,4,5-η)-1,2,3,4,5-pentamethyl-2,4-cyclopentadien-1-yl] cobalt (III) 2-nitrate, triaqua[(1,2,3,4,5-η)-1,2,3,4,5-pentamethyl-2,4-cyclopentadien-1-yl] rhodium (III) 2-nitrate, triaqua[(1,2,3,4,5-η)-1,2,3,4,5-pentamethyl-2,4-cyclopentadien-1yl] iridium (III) 2-nitrate, triaqua[(1,2,3,4,5-η)-1,2,3,4,5-pentamethyl-2,4-cyclopentadien-1-yl] iron (II) nitrate, triaqua[(1,2,3,4,5-η)-1,2,3,4,5-pentamethyl-2,4-cyclopentadien-1-yl] ruthenium (II) nitrate, triaqua[(1,2,3,4,5-η)-1,2,3,4,5-pentamethyl-2,4-cyclopentadien-1-yl] osmium (II) nitrate, triaqua[(1,2,3,4,5-η)-1,2,3,4,5-pentamethyl-2,4-cyclopentadien-1-yl] cobalt (III) bistrifluoromethanesulfonate, triaqua[(1,2,3,4,5-η)-1,2,3,4,5-pentamethyl-2,4-cyclopentadien-1-yl] rhodium (III) bistrifluoromethanesulfonate, triaqua[(1,2,3,4,5-η)-1,2,3,4,5-pentamethyl-2,4-cyclopentadien-1-yl] iridium (III) bistrifluoromethanesulfonate, triaqua [(1,2,3,4,5-η)-1,2,3,4,5-pentamethyl-2,4-cyclopentadien-1-yl] iron (II) trifluoromethanesulfonate, triaqua[(1,2,3,4,5-η)-1,2,3,4,5-pentamethyl-2,4-cyclopentadien-1-yl] ruthenium (II) trifluoromethanesulfonate, triaqua[(1,2,3,4,5-η)-1,2,3,4,5-pentamethyl-2,4-cyclopentadien-1-yl] osmium (II) trifluoromethanesulfonate, triaqua[(1,2,3,4,5-η)-1,2,3,4,5-pentamethyl-2,4-cyclopentadien-1-yl] cobalt (III) 2-perchlorate, triaqua[(1,2,3,4,5-η)-1,2,3,4,5-pentamethyl-2,4-cyclopentadien-1-yl] rhodium (III) 2-perchlorate, triaqua[(1,2,3,4,5-η)-1,2,3,4,5-pentamethyl-2,4-cyclopentadien-1-yl] iridium (III) 2-perchlorate, triaqua[(1,2,3,4,5-η)-1,2,3,4,5-pentamethyl-2,4-cyclopentadien-1-yl] iron (II) perchlorate, triaqua[(1,2,3,4,5-η)-1,2,3,4,5-pentamethyl-2,4-cyclopentadien-1-yl] ruthenium (II) perchlorate, triaqua[(1,2,3,4,5-η)-1,2,3,4,5-pentamethyl-2,4-cyclopentadien-1-yl] osmium (II) perchlorate, triaqua[(1,2,3,4,5-η)-1,2,3,4,5-pentamethyl-2,4-cyclopentadien-1-yl] cobalt (III) bis(tetrafluoroborate), triaqua[(1,2,3,4,5-η)-1,2,3,4,5-pentamethyl-2,4-cyclopentadien-1-yl] rhodium (III) bis(tetrafluoroborate), triaqua[(1,2,3,4,5-η)-1,2,3,4,5-pentamethyl-2,4-cyclopentadien-1-yl] iridium (III) bis(tetrafluoroborate), triaqua[(1,2,3,4,5-η)-1,2,3,4,5-pentamethyl-2,4-cyclopentadien-1-yl] iron (II) tetrafluoroborate, triaqua[(1,2,3,4,5-η)-1,2,3,4,5-pentamethyl-2,4-cyclopentadien-1-yl] ruthenium (II) tetrafluoroborate, triaqua[(1,2,3,4,5-η)-1,2,3,4,5-pentamethyl-2,4-cyclopentadien-1-yl] osmium (II) tetrafluoroborate, triaqua[(1,2,3,4,5-η)-2,4-cyclopentadien-1-yl] bispyridine cobalt (III) 2-perchlorate, triaqua[(1,2,3,4,5-η)-2,4-cyclopentadien-1-yl] bispyridine rhodium (III) 2-perchlorate, triaqua[(1,2,3,4,5-η)-2,4-cyclopentadien-1-yl] bispyridine iridium (III) 2-perchlorate, aqua (2,2'-bipyridine)[(1,2,3,4,5-η)-2,4-cyclopentadien-1-yl] cobalt (III) 2-perchlorate, aqua(2,2'-bipyridine) [(1,2,3,4,5-

η)-2,4-cyclopentadien-1-yl] rhodium (III) 2-perchlorate, aqua(2,2'-bipyridine) [(1,2,3,4,5-η)-2,4-cyclopentadien-1-yl] iridium (III) 2-perchlorate, aqua(2,2'-bipyridine) [(1,2,3,4,5-η)-2,4-cyclopentadien-1-yl] cobalt (III) 2-perchlorate, aqua(2,2'-bipyridine)[(1,2,3,4,5-η)-2,4-cyclopentadien-1-yl] rhodium (III) 2-perchlorate, aqua(2,2'-bipyridine) [(1,2,3,4,5-η)-2,4-cyclopentadien-1-yl] rhodium (III) 2-perchlorate, and the like.

The transition metal complex represented by General Formula (3) of the present invention can be produced in accordance with the following method for example. In the presence of water having a pH 3.8, ($\eta^5$-tetramethyl cyclopentadienyl) rhodium (III) triaqua complex is reacted with 2,2'-bipyridine to give ($\eta^5$-tetramethyl cyclopentadienyl) rhodium (III) (2,2'-bipyridyl) aqua complex. A reaction temperature is generally from −40 to 200° C., but a preferred reaction temperature is −20 to 100° C. A reaction time varies depending on reaction conditions such as a reaction substrate concentration, a temperature, and the like, but the reaction is generally completed in several hours to 30 hours.

<Transition Metal Complex Represented by General Formula (8)>

In an organic metal complex represented by General Formula (8), examples of $R^1$, $R^2$, $R^3$, $R^4$, $R^5$, or $R^6$ lower alkyl group include a methyl group, an ethyl group, a propyl group, a butyl group, a pentyl group, a hexyl group, an isopropyl group, a t-butyl group, an isoamyl group, a cyclopentyl group, a cyclohexyl group, and the like.

Further, any element may be used as M element in Group VIII of the periodic table as long as the element is capable of forming a benzene ring. Preferred is Ru.

Further, examples of $X^1$, $X^2$, or $X^3$ ligand include $H_2O$, halogen, a solvent molecule, and the like. Examples of the solvent molecule include methanol, ethanol, acetonitrile, tetrahydrofuran, pyridine, dimethylsulfoxide, dimethylformamide, and the like. Note that, it is preferable that $X^1$, $X^2$, and $X^3$ ligands in General Formula (8) are entirely $H_2O$.

Examples of an anion species represented by Y include carboxylic acid ion such as formic acid and acetic acid, sulfate ion, fluoride ion, chloride ion, bromide ion, iodide ion, triflurt ion, perchloriante ion, perbromate ion, periodate ion, tetrafluoro borate ion, hexafluoro phosphate ion, thiocyanate ion, and the like.

Specific examples of the organic metal complex represented by General Formula (8) include triaqua-[(1,2,3,4,5,6-$\eta^6$)-hexamethylbenzene-1-yl] ruthenium (II) 2-hexafluorophosphate, triaqua-[(1,2,3,4,5,6-$\eta^6$)-hexamethylbenzene-1-yl] ruthenium (II) 2-tetrafluoroborate, triaqua-[(1,2,3,4,5,6-$\eta^6$)-hexamethylbenzene-1-yl] ruthenium (II) sulphate, triaqua-[(1,2,3,4,5,6-$\eta^6$)-hexamethylbenzene-1-yl] ruthenium (II) 2-formate, triaqua-[(1,2,3,4,5,6-$\eta^6$)-cymene-1-yl] ruthenium (II) 2-hexafluorophosphate, triaqua-[(1,2,3,4,5,6-$\eta^6$)-cymene-1-yl] ruthenium (II) sulphate, triaqua-[(1,2,3,4,5,6-$\eta^6$)-cymene-1-yl] ruthenium (II) 2-formate, triaqua-[(1,2,3,4,5,6-$\eta^6$)-cymene-1-yl] ruthenium (II) 2-tetrafluoroborate, aqua-2,2'-bipyridyl-[(1,2,3,4,5,6-$\eta^6$)-hexamethylbenzene-1-yl] ruthenium (II) 2-hexafluorophosphate, aqua-2,2'-bipyridyl-[(1,2,3,4,5,6-$\eta^6$)-hexamethylbenzene-1-yl] ruthenium (II) 2-tetrafluoroborate, aqua-2,2'-bipyridyl-[(1,2,3,4,5,6-$\eta^6$)-hexamethylbenzene-1-yl] ruthenium (II) sulphate, aqua-2,2'-bipyridyl-[(1,2,3,4,5,6-$\eta^6$)-hexamethylbenzene-1-yl] ruthenium (II) formate, aqua-2,2'-bipyridyl-[(1,2,3,4,5,6-$\eta^6$)-cymene-1-yl] ruthenium (II) hexafluorophosphate, aqua-2,2'-bipyridyl-[(1,2,3,4,5,6-$\eta^6$)-cymene-1-yl] ruthenium (II) sulphate, aqua-2,2'-bipyridyl-[(1,2,3,4,5,6-$\eta^6$)-cymene-1-yl] ruthenium (II) formate, aqua-2,2'-bipyridyl-[(1,2,3,4,5,6-$\eta^6$)-cymene-1-yl] ruthenium (II) tetrafluoroborate, and the like. Preferred are triaqua-[(1,2,3,4,5,6-$\eta^6$)-hexamethylbenzene-1-yl] ruthenium (II) sulphate, triaqua-[(1,2,3,4,5,6-$\eta^6$)-cymene-1-yl] ruthenium (II) sulfate, and the like.

The organic metal complex represented by General Formula (8) of the present invention can be produced in accordance with the following method. That is, [(1,2,3,4,5,6-$\eta^6$)-hexamethylbenzene-1-yl] ruthenium (II) trichloride is reacted with sulfate in the presence of water having a pH 3.8 to give triaqua-[(1,2,3,4,5,6-$\eta^6$)-hexamethylbenzene-1-yl] ruthenium (II) sulphate.

<Hydration of Acetylene-Carboxylic Acids>

One mode of the present invention is a method for synthesis of keto acids (including keto acid and keto acid derivative) which method is characterized by hydration of acetylene-carboxylic acids in the presence of at least one compound selected from a group consisting of a metal salt represented by General Formula (1) (hereinafter, the metal salt is referred to as "metal salt 1"), a transition metal complex represented by General Formula (2) (hereinafter, the transition metal complex is referred to as "transition metal complex 2"), a transition metal complex represented by General Formula (3) (hereinafter, the transition metal complex is referred to as "transition metal complex 3"), and a transition metal complex represented by General Formula (8) (hereinafter, the transition metal complex is referred to as "transition metal complex 4"). According to the method, it is possible to efficiently perform hydration of acetylene-carboxylic acids under mild conditions. Hereinafter, a compound including keto acid and keto acid derivative is referred to as "keto acids". The "keto acid derivative" is not particularly limited, but examples thereof include keto-acid ester.

An example of acetylene-carboxylic acid used in the hydration of the present invention is a carbonyl compound represented by General Formula (6)

$$R^1CCCOOR^2 \qquad (6)$$

where each of $R^1$ and $R^2$ independently represents a hydrogen atom, an alkyl group which may be substituted and whose carbon number is 1-10, an aryl group which may be substituted and whose carbon number is 1-10, an alkoxycarbonyl group which may be substituted and whose carbon number is 1-10, or an aryloxycarbonyl group which may be substituted and whose carbon number is 1-10.

Examples of the alkyl group represented by $R^1$ or $R^2$ of the acetylene-carboxylic acids represented by General Formula (6) include a methyl group, an ethyl group, an n-propyl group, an i-propyl group, an n-butyl group, a t-butyl group, an n-hexyl group, a cyclohexyl group, an n-heptyl group, an n-octyl group, an n-nonyl group, an n-decile group, and the like.

Specific examples of the acetylene-carboxylic acids represented by General Formula (6) include propionic acid, propionate methyl, propionate ethyl, propionate isopropyl, t-butyl propionate, acetylenedicarboxylate, dimethyl acetylenedicarboxylate, diethyl acetylenedicarboxylate, diisopropyl acetylenedicarboxylate, acetylenedicarboxylate di t-butyl, 2-butynate, 2-butynate methyl, 2-butynate ethyl, 2-butynate isopropyl, 2-butynate t-butyl, 2-pentynate, 2-pentynate methyl, 2-pentynate ethyl, 2-pentynate isopropyl, 2-pentynate t-butyl, 2-hyxynate, 2-hexynate methyl, 2-hexynate ethyl, 2-hexynate isopropyl, 2-hexynate t-butyl, 2-heptynate, 2-heptynate methyl, 2-heptynate ethyl, 2-heptynate isopropyl, 2-heptynate t-butyl, 2-octynate, 2-octynate methyl, 2-octynate ethyl, 2-octynate isopropyl, 2-octynate t-butyl, 2-nonyate, 2-nonyoate methyl, 2-nonyoate ethyl, 2-nonyoate isopropyl, 2-nonyoate t-butyl, phenylpropiolate, phenylpropiolate methyl, phenylpropiolate ethyl, phenylpropiolate isopropyl, phenylpropiolate t-butyl, and the like.

As the acetylene-carboxylic acids represented by General Formula (6), commercially available acetylene-carboxylic acids may be used. Examples of the commercially available acetylene-carboxylic acids are products of Nacalai Tesque Co., Ltd, Tokyo Chemical Industry Co., LTD, and Sigma Aldrich Japan K.K.

The hydration of the present invention allows for synthesis of keto acid and keto acid derivative corresponding to the acetylene-carboxylic acids represented by General Formula (6).

Amounts of the metal salt 1, the transition metal complex 2, the transition metal complex 3, and the transition metal complex 4 which are used in the hydration of the present invention are not particularly limited and are suitably set in consideration for optimal conditions. Generally, a molar ratio with respect to acetylene-carboxylic acids serving as starting material is within a range of 1 to 1/100,000 roughly, preferably within a range of 1/50 to 1/10,000 roughly, in performing the hydration.

The hydration of the present invention is performed in the presence of or in the absence of an organic solvent dissolving the starting material. Examples of the "organic solvent dissolving the starting material" include: a polar solvent such as methanol, ethanol, acetonitrile, dimethylformamide, dimethylsulfoxide, and tetrahydrofuran; aliphatic hydrocarbon solvent such as hexane, cyclohexane, and heptane; aromatic hydrocarbon solvent such as benzene, toluene, and xylene; halogenated aromatic hydrocarbon solvent such as chlorobenzene and dichlorobenzene; and a mixture thereof. Basically, in view of the catalytic activity and the product selectivity, it is more preferable to perform the hydration in the absence of the organic solvent. However, depending on cases, hydration in the presence of the organic solvent dissolving the starting material allows the reaction to proceed.

In the hydration of the present invention, the pH is not particularly limited and is suitably set in consideration for optimal conditions. However, for such reason that the metal salt 1, the transition metal complex 2, the transition metal complex 3, and the transition metal complex 4 can stably exist in water, the pH in the hydration of the present invention is preferably 1 to 5, more preferably 1 to 3.

The hydration of the present invention is performed generally at a temperature ranging from −90 to 200° C., but preferably from 20 to 100° C., more preferably from 80 to 100° C. Also the reaction temperature is suitably set in consideration for optimal conditions.

Further, a reaction time varies depending on reaction conditions such as a reaction substrate concentration, a temperature, and the like, but it is general that the reaction is completed in several hours to about 30 hours.

How to isolate a target product and how to purify the target product after completion of the hydration of the present invention are not particularly limited, and the isolation and the purification can be carried out by suitably adopting known methods. For example, after completion of the hydration, the solvent and an unreacted raw material are distilled and the distilled solvent and material are washed with water and evaporated. Further, the metal salt or the transition metal complex used as a catalyst can be removed by the washing with water, the evaporation, and a treatment such as adsorption and the like. Further, the hydration is performed while the metal salt or the transition metal complex serving as a catalyst is held by a suitable support such as silica gel, activated white clay, and the like, so that the metal salt or the transition metal complex fixed on the support can be removed by filtration after completion of the reaction. Further, the thus collected metal salt or transition metal complex can be reused.

<Reductive Amination of Keto Acids>

The method according to the present invention for synthesis of amino acids (including amino acid and amino acid derivative) (hereinafter, this method is suitably referred to as "amino acid synthesis method of the present invention") may include the step of performing reductive amination of keto acids in the presence of the transition metal complex 3 and a hydrogen and nitrogen atom donor. Hereinafter, a compound including amino acid and amino acid derivative is referred to as "amino acids". Examples of the "amino acid derivative" include amino-acid ester and N-alkyl amino acid obtained by alkylation of an amino group.

An example of the keto acids used in the reductive amination is keto acids represented by General Formula (7)

$$R^1COCOOR^2 \qquad (7)$$

where each of $R^1$ and $R^2$ independently represents a hydrogen atom, an alkyl group which may be substituted and whose carbon number is 1-10, an aryl group which may be substituted and whose carbon number is 1-10, an alkoxycarbonyl group which may be substituted and whose carbon number is 1-10, or an aryloxycarbonyl group which may be substituted and whose carbon number is 1-10.

Examples of the alkyl group represented by $R^1$ or $R^2$ of the keto acids represented by General Formula (7) include a methyl group, an ethyl group, an n-propyl group, an i-propyl group, an n-butyl group, a t-butyl group, an n-hexyl group, a cyclohexyl group, an n-heptyl group, an n-octyl group, an n-nonyl group, an n-decile group, and the like.

Specific examples of the keto acid derivative represented by General Formula (7) include pyruvic acid, methyl pyruvate, ethyl pyruvate, isopropyl pyruvate, t-butyl pyruvate, phenyl pyruvate, 2-oxobutanate, 2-oxobutanate methyl, 2-oxobutanate ethyl, 2-oxobutanate isopropyl, 2-oxobutanate t-butyl, 3-methyl-2-oxobutanate, 3-methyl-2-oxobutanate methyl, 3-methyl-2-oxobutanate ethyl, 3-methyl-2-oxobutanate isopropyl, 3-methyl-2-oxobutanate t-butyl, 2-oxopentanate, 2-oxopentanate methyl, 2-oxopentanate ethyl, 2-oxopentanate isopropyl, 2-oxopentanate, 3-methyl-2-oxopentanate, 3-methyl-2-oxopentanate methyl, 3-methyl-2-oxopentanate ethyl, 3-methyl-2-oxopentanate isopropyl, 3-methyl-2-oxopentanate t-butyl, 4-methyl-2-oxopentanate, 4-methyl-2-oxopentanate methyl, 4-methyl-2-oxopentanate ethyl, 4-methyl-2-oxopentanate isopropyl, 4-methyl-2-oxopentanate t-butyl, 2-oxohexanate, 2-oxohexanate, 2-oxohexanate methyl, 2-oxohexanate ethyl, 2-oxohexanate isopropyl, 2-oxohexanate t-butyl, 2-oxooctanate, 2-oxooctanate methyl, 2-oxooctanate ethyl, 2-oxooctanate isopropyl, 2-oxooctanate t-butyl, phenyl pyruvate, phenyl pyruvate methyl, phenyl pyruvate ethyl, phenyl pyruvate isopropyl, phenyl pyruvate t-butyl, glyoxylic acid, glyoxylate methyl, glyoxylate ethyl, glyoxylate isopropyl, glyoxyl t-butyl, phenyl glyoxylic acid, phenyl glyoxylate methyl, phenyl glyoxylate ethyl, phenyl glyoxylate isopropyl, phenyl glyoxylate t-butyl, 2-oxoglutaric acid, and the like.

The keto acids represented by General Formula (7) of the present invention can be obtained by oxidization of alcohol part (hydroxyl group) of hydroxy acid for example.

The reductive amination in the amino acid synthesis method of the present invention allows for synthesis of amino acids corresponding to the keto acids represented by General Formula (7).

The "hydrogen and nitrogen atom donor" used in the reductive amination in the amino acid synthesis method of the present invention is not particularly limited as long as the donor can provide hydrogen atoms and nitrogen atoms to the keto acid derivative. Examples thereof include formic ammonium or salt thereof, ammonia, N-alkylamines (e.g., dimethylamine, diethylamine, diisopropylamine, and di-t-butylamine), and the like.

An amount of the transition metal complex 3 used in the reductive amination in the amino acid synthesis method of the present invention is not particularly limited and is suitably set in consideration for optimal conditions. Generally, a molar ratio with respect to keto acids serving as starting material is within a range of 1 to $1/100,000$ roughly, preferably within a range of $1/50$ to $1/10,000$ roughly, in performing the hydration.

The reductive amination of the present invention is performed in the presence of or in the absence of the organic solvent dissolving the starting material. Examples of the "organic solvent dissolving the starting material" include: a polar solvent such as methanol, ethanol, acetonitrile, dimethylformamide, dimethylsulfoxide, and tetrahydrofuran; aliphatic hydrocarbon solvent such as hexane, cyclohexane, and heptane; aromatic hydrocarbon solvent such as benzene, toluene, and xylene; halogenated aromatic hydrocarbon solvent such as chlorobenzene and dichlorobenzene; and a mixture thereof. Basically, in view of the catalytic activity and the product selectivity, it is more preferable to perform the hydration in the absence of the organic solvent. However, depending on cases, hydration in the presence of the organic solvent dissolving the starting material allows the reaction to proceed.

In the reductive amination in the amino acid synthesis method of the present invention, the pH is not particularly limited and is suitably set in consideration for optimal conditions. However, for such reason that a hydride complex generated by reaction of the transition metal complex 3 and formic acid ions is stable when the pH is within the aforementioned range (particularly, pH 4.5 to 7), the pH in the reductive amination is preferably 1 to 10, more preferably 3 to 7, still more preferably 4.5 to 7. Note that, the hydride complex is a catalytically active species of the reductive amination.

The reductive amination in the amino acid synthesis method of the present invention is performed generally at a temperature ranging from 0 to 200° C., but preferably from 60 to 80° C. Also the reaction temperature is suitably set in consideration for optimal conditions.

Further, a reaction time varies depending on reaction conditions such as a reaction substrate concentration, a temperature, and the like, but it is general that the reaction is completed in several hours to about 30 hours.

How to isolate a target product and how to purify the target product after completion of the hydration of the present invention are not particularly limited, and the isolation and the purification can be carried out by suitably adopting known methods. For example, after completion of the hydration, the solvent and an unreacted raw material are distilled and the distilled solvent and material are washed with water and evaporated. Further, the metal salt or the transition metal complex used as a catalyst can be removed by the washing with water, the evaporation, and a treatment such as adsorption and the like. Further, hydration is performed while the metal salt or the transition metal complex serving as a catalyst is held by a suitable support such as silica gel, activated white clay, and the like, so that the metal salt or the transition metal complex fixed on the support can be removed by filtration after completion of the reaction. Further, the thus collected metal salt or transition metal complex can be reused.

<Method for Synthesis of Amino Acids from Acetylene-Carboxylic Acids With a Catalyst in the Same Reaction Vessel (One-Pot Synthesis)>

One embodiment according to the present invention for synthesis of amino acids is a method which is characterized in that acetylene-carboxylic acids are hydrated in the presence of at least one compound selected from a group consisting of the metal salt 1, the transition metal complex 2, the transition metal complex 3, and the transition metal complex 4, and the transition metal complex catalyst 3 and the hydrogen and nitrogen atom donor are added to a reaction system of the hydrated acetylene-carboxylic acids to cause a reaction thereof. That is, one embodiment of the method according to the present invention for synthesis of amino acids is a method in which the "hydration of acetylene-carboxylic acids" and the "reductive amination of keto acids" are sequentially performed in a single reaction vessel to synthesize amino acids from the acetylene-carboxylic acids.

The alkyl group represented by $R^1$ or $R^2$ of the acetylene-carboxylic acids represented by General Formula (6) is an alkyl group whose carbon number is 1-10. Specific examples thereof include a methyl group, an ethyl group, an n-propyl group, an i-propyl group, an n-butyl group, a t-butyl group, an n-hexyl group, a cyclohexyl group, an n-heptyl group, an n-octyl group, an n-nonyl group, an n-decile group, and the like. These starting materials are used to sequentially perform reactions of the acetylene-carboxylic acids into amino acids.

Specific examples of the acetylene-carboxylic acids used in the sequential reactions include propiolic acids, propiolate methyl, propiolate ethyl, propiolate isopropyl, propiolate t-butyl, acetylenedicarboxylate, acetylenedicarboxylate dimethyl, acetylenedicaboxylate diethyl, acetylenedicarboxylate diisopropyl, acetylenedicarboxylate di t-butyl, 2-butynate, 2-butynate methyl, 2-butynate ethyl, 2-butynate isopropyl, 2-butynate t-butyl, 2-pentynate, 2-pentynate methyl, 2-pentynate ethyl, 2-pentynate isopropyl, 2-pentynate t-butyl, 2-hyxynate, 2-hexynate methyl, 2-hexynate ethyl, 2-hexynate isopropyl, 2-hexynate t-butyl, 2-heptynate, 2-heptynate methyl, 2-heptynate ethyl, 2-heptynate isopropyl, 2-heptynate t-butyl, 2-octynate, 2-octynate methyl, 2-octynate ethyl, 2-octynate isopropyl, 2-octynate t-butyl, 2-nonyate, 2-nonyoate methyl, 2-nonyoate ethyl, 2-nonyoate isopropyl, 2-nonyoate t-butyl, phenylpropiolate, phenylpropiolate methyl, phenylpropiolate ethyl, phenylpropiolate isopropyl, phenylpropiolate t-butyl, and the like.

As the acetylene-carboxylic acids represented by General Formula (6), commercially available acetylene-carboxylic acids may be used. Examples of the commercially available acetylene-carboxylic acids are products of Nacalai Tesque Co., Ltd, Tokyo Chemical Industry Co., Ltd, and Sigma Aldrich Japan K.K.

The pH in the sequential reactions of the hydration and the reductive amination of the present invention is suitably set at the hydration stage to be within the range described in <Hydration of acetylene-carboxylic acids> and at the reductive amination stage to be within the range described in <Reductive amination of keto acids>.

Amounts of the metal salt 1, the transition metal complex 2, the transition metal complex 3, and the transition metal complex 4 which are used in the method of the present invention for synthesis of amino acids are not particularly limited and are suitably set in consideration for optimal conditions. Generally, a molar ratio with respect to keto acids serving as starting material is within a range of 1 to $1/100,000$ roughly, preferably within a range of $1/50$ to $1/10,000$ roughly, in performing the reactions.

The amino acid synthesis of the present invention through the sequential reactions of the hydration and the reductive amination is carried out in the presence of or in the absence of organic solvent dissolving the starting material. Examples of the "organic solvent dissolving the starting material" include: a polar solvent such as methanol, ethanol, acetonitrile, dimethylformamide, dimethylsulfoxide, and tetrahydrofuran; aliphatic hydrocarbon solvent such as hexane, cyclohexane, and heptane; aromatic hydrocarbon solvent such as benzene, toluene, and xylene; halogenated aromatic hydrocarbon solvent such as chlorobenzene and dichlorobenzene; and a mixture thereof. Basically, in view of the catalytic activity and the product selectivity, it is more preferable to perform the hydration in the absence of the organic solvent. However, depending on cases, hydration in the presence of the organic solvent dissolving the starting material allows the reaction to proceed.

The amino acid synthesis of the present invention through the sequential reactions of the hydration and the reductive amination is performed generally at a temperature of 0 to 100° C., but preferably at a temperature of 60 to about 80° C. Also a reaction temperature is suitably set in consideration for optimal conditions.

Further, a reaction time varies depending on reaction conditions such as a reaction substrate concentration, a temperature, and the like, but the reaction is generally completed in several hours to 30 hours.

If amino acids are produced from acetylene-carboxylic acids in one-pot synthesis (that is, in a sequential manner with a single reaction vessel) in this way, it is not necessary to isolate and purify keto acids, i.e., intermediate products of the amino acid synthesis. This makes it possible to realize such advantage that amino acids can be produced at lower cost and in a shorter time.

<Method for Synthesis of Amino Acids From Acetylene-Carboxylic Acids With a Catalyst Synthesized in the Same Reaction Vessel in-situ (Tandem Synthesis)>

One embodiment according to the present invention for synthesis of amino acids may be a method characterized in that acetylene-carboxylic acids are hydrated in the presence of the transition metal complex 2, the transition metal complex 3, and the transition metal complex 4, and the hydrogen and nitrogen atom donor is added to a reaction system of the hydrated acetylene-carboxylic acids to cause a reaction thereof.

Further, one embodiment according to the present invention for synthesis of amino acids may be a method characterized in that acetylene-carboxylic acids are hydrated in the presence of the metal salt 1, and the organic ligands represented by General Formula (4) and General Formula (5) and the hydrogen and nitrogen atom donor are added to a reaction system of the hydrated acetylene-carboxylic acids to cause a reaction thereof.

That is, the method is such that the "hydration of acetylene-carboxylic acids" and the "reductive amination of keto acids" are sequentially performed to synthesize amino acids from the acetylene-carboylic acids. The substances and reaction conditions adopted in the synthesis are the same as in the aforementioned one-pot synthesis, but the tandem synthesis is characterized in that a metal catalyst is formed in the reaction system by adding the ligands and the reaction is performed with the metal catalyst. This makes it possible to realize such advantage that the tandem synthesis does not require any expensive metal catalyst in performing the sequential reactions.

Examples of $R^1$, $R^2$, $R^3$, $R^4$, or $R^5$ lower alkyl group in the organic ligand represented by General Formula (4) and $R^1$, $R^2$, $R^3$, $R^4$, $R^5$, $R^6$, $R^7$, and $R^8$ lower alkyl group in the organic ligand represented by General Formula (5) include an alkyl group whose carbon number is 1-6, specifically, a methyl group, an ethyl group, a propyl group, a butyl group, a pentyl group, a hexyl group, an isopropyl group, a t-butyl group, an isoamyl group, a cyclopentyl group, a cyclohexyl group, and the like.

Specific examples of the organic ligand represented by General Formula (4) include 1,2,3,4,5-pentamethyl-1,3-cyclopentadiene, 1,2,3,4,5-pentaethyl-1,3-cyclopentadiene, 1,2,3,4,5-pentaisopropyl-1,3-cyclopentadiene, 1,2,3,4,5-penta-t-butyl-1,3-cyclopentadiene, 1,2,3,4,5-pentaphenyl-1,3-cyclopentadiene, trimethyl (2,3,4,5-tetramethyl-2,4-cyclopentadiene-1-yl) silane, trimethyl (2,3,4,5-tetraethyl-2,4-cyclopentadiene-1-yl) silane, trimethyl (2,3,4,5-tetraisopropyl-2,4-cyclopentadiene-1-yl) silane, trimethyl (2,3,4,5-tetra-t-butyl-2,4-cyclopentadiene-1-yl) silane, trimethyl (2,3,4,5-tetraphenyl-2,4-cyclopentadiene-1-yl) silane, chlorodimethyl (2,3,4,5-tetramethyl-2,4-cyclopentadiene-1-yl) silane, chlorodimethyl (2,3,4,5-tetraethyl-2,4-cyclopentadiene-1-yl) silane, chlorodimethyl (2,3,4,5-tetraisopropyl-2,4-cyclopentadiene-1-yl) silane, chlorodimethyl (2,3,4,5-tetra-t-butyl-2,4-cyclopentadiene-1-yl) silane, chlorodimethyl (2,3,4,5-tetraphenyl-2,4-cyclopentadiene-1-yl) silane, 5-((t-butylamino) dimethylsilyl)-1,2,3,4-tetramethyl-1,3-cyclopentadiene, 5-((t-butylamino) dimethylsilyl)-1,2,3,4-tetraethyl-1,3-cyclopentadiene, 5-((t-butylamino) dimethylsilyl)-1,2,3,4-tetraisopropyl-1,3-cyclopentadiene, 5-((t-butylamino) dimethylsilyl)-1,2,3,4-tetra-t-butyl-1,3-cyclopentadiene, 5-((t-butylamino) dimethylsilyl)-1,2,3,4-tetraphenyl-1,3-cyclopentadiene, 1-(2,3,4,5-tetramethyl-1,3-cyclopentadiene-1-ylethanone, [(2,3,4,5-tetramethyl-2,4-cyclopentadiene-1-yl) methyl]-benzene, 1,1',1",1''', 1''''-[(1,3-cyclopentadiene-1,2,3,4,5-pentayl)pentaquis (methylene)] pentaquisbenzene, 1,2,4,5-tetramethyl-3-propyl-1,3-cyclopentadiene, 2,3,4,5-tetraphenyl-2,4-cyclopentadiene-1-ol, and the like.

Specific examples of the organic ligand represented by General Formula (5) include 2,2'-bipyridine, 1,10-phenanthroline, 2,2'-biquinoline, 2,2'-bi-1,8-naphthyridine, 6,6'-dimethyl-2,2'-bipyridine, 6,6'-dicarbonitrile-2,2'-bipyridine, 6,6'-bis(chloromethyl)-2,2' bipyridine, 2,9-dimethyl-1,10-phenanthroline, 4,4'-(2,9-dimethyl-1,10-phenanthroline-4,7-diiryl)bis-benzene sulfonic acid, 2,9-dimethyl-N-(2,4,6-trinitrophenyl)-1,10-phenanthroline-5-amine, 1,10-phenanthroline-2,9-dicarboxyaldehyde, 2,9-dicarboxy-1,10-phenanthroline, 2,9-dicarboxy-1,10-phenanthroline, 2,9-dimethyl 4,7-diphenyl-1,10-phenanthroline, (2,2'-biquinoline)-4,4'-dicarboxylic acid, (2,2'-biquinoline)-4'-carboxylic acid, 4,4'-dimethyl-2,2'-biquinoline, 5,5'-dimethyl-2,2'-bipyridine, 5,5'-dicarbonitrile-2,2'-bipyridine, 5,5'-bis(chloromethyl)-2,2' bipyridine, 3,8-dimethyl-1,10-phenanthroline, 4,4'-(3,8-dimethyl-1,10-phenanthroline-4,7-diiryl)bis-benzene sulfonic acid, 1,10-phenanthroline-2,9-dicarboxyaldehyde, 3,8-dicarboxy-1,10-phenanthroline, 3,8-dicarboxy-1,10-phenanthroline, 3,8-dimethyl 4,7-diphenyl-1,10-phenanthroline, 4,4'-dimethyl-2,2'-bipyridine, 4,4'-dimethoxy-2,2'-bipyridine, 4,4'-dicarbonitrile-2,2'-bipyridine, 5,5'-bis(chloromethyl)-2,2' bipyridine, 4,7-dimethyl-1,10-phenanthroline, 1,10-phenanthroline-4,7-dicarboxyaldehyde, 4,7-dicarboxy-1,10-phenanthroline, and the like.

As the organic ligands represented by General Formula (4) and General Formula (5), commercially available organic ligands may be used. Examples of the commercially available organic ligands are products of Nacalai Tesque Co., Ltd, Tokyo Chemical Industry Co., Ltd, and Sigma Aldrich Japan K.K.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

EXAMPLES

The following Examples will further detail the present invention, but the present invention is not limited to the Examples.

<1. Example of synthesis of keto acids (α- or β-keto acids)>

Acetylene-carboxylic acids were hydrated in the presence of various kinds of metal salts or transition metal complexes to synthesize keto acids (α- or β-keto acids). Each of FIG. 1(a) and FIG. 1(b) shows a reaction formula of the hydration. Note that, when water-soluble acetylene-carboxylic acids were hydrated, α-keto acids were synthesized (FIG. 1(a)), and when water-insoluble acetylene-carboxylic acids were hydrated, β-keto acids were synthesized (FIG. 1(b)). For convenience in descriptions, a reaction path shown in FIG. 1(a) is referred to as "Path A" and a reaction path shown in FIG. 1(b) is referred to as "Path C".

Example 1

0.5 mmol of water-soluble acetylene carboxylic acids whose $R^1$ and $R^2$ are H in FIG. 1(a) was mixed with 2 mL of aqueous solution containing 5.0 μmol of ruthenium trichloride, and the mixture was reacted at the pH 2.0 at 80° C. under argon atmosphere for 12 hours. The resulting mixture was condensed to give a product. The product was analyzed by $^1$H NMR.

Example 2

0.5 mmol of water-soluble acetylene carboxylic acids whose $R^1$ and $R^2$ are H in FIG. 1(a) was mixed with 2 mL of aqueous solution containing 5.0 μmol of rhodium trichloride, and the mixture was reacted at the pH 2.0 at 80° C. under argon atmosphere for 12 hours. The resulting mixture was condensed to give a product. The product was analyzed by $^1$H NMR.

Example 3

0.5 mmol of water-soluble acetylene carboxylic acids whose $R^1$ and $R^2$ are H in FIG. 1(a) was mixed with 2 mL of aqueous solution containing 3.1 mg (2.5 μmol) of di[triaqua {2,6-di(phenylthiomethyl)pyridine} ruthenium (III)] 3-sulphate, and the mixture was reacted at the pH 2.0 at 80° C. under argon atmosphere for 12 hours. The resulting mixture was condensed to give a product. The product was analyzed by $^1$H NMR.

Example 4

0.5 mmol of water-soluble acetylene carboxylic acids whose $R^1$ and $R^2$ are H in FIG. 1(a) was mixed with 2 mL of aqueous solution containing 3.1 mg (2.5 μmol) of di[triaqua {2,6-di(phenylthiomethyl)pyridine} rhodium (III)] 3-sulphate, and the mixture was reacted at the pH 2.0 at 80° C. under argon atmosphere for 12 hours. The resulting mixture was condensed to give a product. The product was analyzed by $^1$H NMR.

Comparative Example 1

The same operation as in Examples 1 to 4 except that $HgSO_4$ was used as a catalyst.

Example 5

0.1 mmol of water-soluble acetylene carboxylic acids whose $R^1$ is COOH and $R^2$ is H in FIG. 1(a) was mixed with 2 mL of aqueous solution containing 5.0 μmol of ruthenium trichloride, and the mixture was reacted at the pH 2.0 at 80° C. under argon atmosphere for 12 hours. The resulting mixture was condensed to give a product. The product was analyzed by $^1$H NMR.

Example 6

0.1 mmol of water-soluble acetylene carboxylic acids whose $R^1$ is COOH and $R^2$ is H in FIG. 1(a) was mixed with 2 mL of aqueous solution containing 5.0 μmol of rhodium trichloride, and the mixture was reacted at the pH 2.0 at 80° C. under argon atmosphere for 12 hours. The resulting mixture was condensed to give a product. The product was analyzed by $^1$H NMR.

Example 7

0.1 mmol of water-soluble acetylene carboxylic acids whose $R^1$ is COOH and $R^2$ is H in FIG. 1(a) was mixed with 2 mL of aqueous solution containing 3.1 mg (2.5μmol) of di[triaqua {2,6-di(phenylthiomethyl)pyridine} ruthenium (III)] 3-sulphate, and the mixture was reacted at the pH 2.0 at 80° C. under argon atmosphere for 12 hours. The resulting mixture was condensed to give a product. The product was analyzed by $^1$H NMR.

Example 8

0.1 mmol of water-soluble acetylene carboxylic acids whose $R^1$ is COOH and $R^2$ is H in FIG. 1(a) was mixed with 2 mL of aqueous solution containing 3.1 mg (2.5 μmol) of di[triaqua {2,6-di(phenylthiomethyl)pyridine} rhodium (III)] 3-sulphate, and the mixture was reacted at the pH 2.0 at 80° C. under argon atmosphere for 12 hours. The resulting mixture was condensed to give a product. The product was analyzed by $^1$H NMR.

Comparative Example 2

The same operation as in Examples 5 to 8 except that $HgSO_4$ was used as a catalyst.

Example 9

0.1 mmol of water-soluble acetylene carboxylic acids whose $R^1$ is $CH_3$ and $R^2$ is H in FIG. 1(a) was mixed with 2 mL of aqueous solution containing 5.0 μmol of ruthenium trichloride, and the mixture was reacted at the pH 2.0 at 80° C. under argon atmosphere for 12 hours. The resulting mixture was condensed to give a product. The product was analyzed by $^1$H NMR.

Example 10

0.1 mmol of water-soluble acetylene carboxylic acids whose $R^1$ is $CH_3$ and $R^2$ is H in FIG. 1(a) was mixed with 2 mL of aqueous solution containing 3.1 mg (2.5 µmol) of di[triaqua {2,6-di(phenylthiomethyl) pyridine} ruthenium (III)] 3-sulphate, and the mixture was reacted at the pH 2.0 at 80° C. under argon atmosphere for 12 hours. The resulting mixture was condensed to give a product. The product was analyzed by $^1$H NMR.

Example 11

0.1 mmol of water-soluble acetylene carboxylic acids whose $R^1$ is $CH_3$ and $R^2$ is H in FIG. 1(a) was mixed with 2 mL of aqueous solution containing 3.1 mg (2.5 µmol) of di[triaqua {2,6-di(phenylthiomethyl)pyridine} rhodium (III)] 3-sulphate, and the mixture was reacted at the pH 2.0 at 80° C. under argon atmosphere for 12 hours. The resulting mixture was condensed to give a product. The product was analyzed by $^1$H NMR.

Comparative Example 3

The same operation as in Examples 9 to 11 except that $HgSO_4$ was used as a catalyst.

Example 12

0.1 mmol of water-insoluble acetylene dicarboxylate ester whose $R^1$ is $CH_3$ and $R^2$ is $C_2H_5$ in FIG. 1(b) was mixed with 2 mL of acetic acid buffer aqueous solution containing 5.0 µmol of ruthenium trichloride, and the mixture was reacted at the pH 4.0 at 80° C. under argon atmosphere for 12 hours. The resulting reaction mixture was extracted and condensed with chloroform to give a product. The product was analyzed by $^1$H NMR.

Example 13

0.1 mmol of water-insoluble acetylene dicarboxylate ester whose $R^1$ is $CH_3$ and $R^2$ is $C_2H_5$ in FIG. 1(b) was mixed with 2 mL of acetic acid buffer aqueous solution containing 5.0 µmol of rhodium trichloride, and the mixture was reacted at the pH 4.0 at 80° C. under argon atmosphere for 12 hours. The resulting reaction mixture was extracted and condensed with chloroform to give a product. The product was analyzed by $^1$H NMR.

Example 14

0.1 mmol of water-insoluble acetylene dicarboxylate ester whose $R^1$ is $CH_3$ and $R^2$ is $C_2H_5$ in FIG. 1(b) was mixed with 2 mL of acetic acid buffer aqueous solution containing 3.1 mg (2.5 µmol) of di[triaqua {2,6-di(phenylthiomethyl)pyridine} ruthenium (III)] 3-sulphate, and the mixture was reacted at the pH 2.0 at 80° C. under argon atmosphere for 12 hours. The resulting reaction mixture was extracted and condensed with chloroform to give a product. The product was analyzed by $^1$H NMR.

Example 15

0.1 mmol of water-insoluble acetylene dicarboxylate ester whose $R^1$ is $CH_3$ and $R^2$ is $C_2H_5$ in FIG. 1(b) was mixed with 2 mL of acetic acid buffer aqueous solution containing 3.1 mg (2.5 µmol) of di[triaqua {2,6-di(phenylthiomethyl)pyridine} rhodium (III)] 3-sulphate, and the mixture was reacted at the pH 2.0 at 80° C. under argon atmosphere for 12 hours. The resulting reaction mixture was extracted and condensed with chloroform to give a product. The product was analyzed by $^1$H NMR.

Comparative Example 4

The same operation as in Examples 13 to 15 except that $HgSO_4$ was used as a catalyst.

[Results of Examples 1 to 15 and Comparative Examples 1 to 4]

Table 1 shows the results.

TABLE 1

| | $R^1$ | $R^2$ | | Cat | Path | TON | mol % | Yield (%) |
|---|---|---|---|---|---|---|---|---|
| Example 1 | H | H | water-soluble | $RuCl_3$ | A | 48 | 1 | 48 |
| Example 2 | H | H | water-soluble | $RhCl_3$ | A | 19 | 1 | 19 |
| Comparative Example 1 | H | H | water-soluble | $HgSO_4$ | A | 4 | 1 | 4 |
| Example 3 | H | H | water-soluble | pincer $Ru^{3+}$ | A | 38 | 1 | 38 |
| Example 4 | H | H | water-soluble | pincer $Rh^{3+}$ | A | 28 | 1 | 28 |
| Example 5 | COOH | H | water-soluble | $RuCl_3$ | A | 14 | 5 | 70 |
| Example 6 | COOH | H | water-soluble | $RhCl_3$ | A | 8 | 5 | 40 |
| Comparative Example 2 | COOH | H | water-soluble | $HgSO_4$ | A | 5 | 5 | 25 |
| Example 7 | COOH | H | water-soluble | pincer $Rh^{3+}$ | A | 15 | 5 | 78 |
| Example 8 | COOH | H | water-soluble | pincer $Rh^{3+}$ | A | 11 | 5 | 57 |
| Example 9 | $CH_3$ | H | water-soluble | $RuCl_3$ | A | 7 | 5 | 35 |
| Comparative Example 3 | $CH_3$ | H | water-soluble | $HgSO_4$ | A | — | 5 | — |
| Example 10 | $CH_3$ | H | water-soluble | pincer $Rh^{3+}$ | A | 6 | 5 | 28 |
| Example 11 | $CH_3$ | H | water-soluble | pincer $Rh^{3+}$ | A | 1 | 5 | 4 |
| Example 12 | $CH_3$ | $C_2H_5$ | water-insoluble | $RuCl_3$ | C | 1 | 5 | 5 |
| Example 13 | $CH_3$ | $C_2H_5$ | water-insoluble | $RhCl_3$ | C | 8 | 5 | 40 |
| Comparative Example 4 | $CH_3$ | $C_2H_5$ | water-insoluble | $HgSO_4$ | C | — | 5 | — |

TABLE 1-continued

|  | R$^1$ | R$^2$ |  | Cat | Path | TON | mol % | Yield (%) |
|---|---|---|---|---|---|---|---|---|
| Example 14 | CH$_3$ | C$_2$H$_5$ | water-insoluble | pincer Rh$^{3+}$ | C | 8 | 5 | 40 |
| Example 15 | CH$_3$ | C$_2$H$_5$ | water-insoluble | pincer Rh$^{3+}$ | C | 4 | 5 | 20 |

In Table 1, "Cat" represents a compound used as a catalyst (the metal salt, the transition metal complex, or HgSO$_4$), "TON" represents a turnover number of the catalyst, "mol %" represents mol % of the catalyst with respect to the acetylene-carboxylic acids, and "Yield (%)" represents an yield of keto acids produced from the acetylene-carboxylic acids. Further, "–" in Table 1 shows that the reaction did not proceed.

The keto-acid yields of Examples 1 to 4 were 4.8 to 12 times higher than that in using mercury sulfate, i.e., a typical mercury catalyst for hydration. In this way, it was confirmed that the catalysts used in Examples have much higher catalytic activity. Particularly, the yields in using ruthenium trichloride and di[triaqua {2.6-di(phenylthiomethyl) pyridine} ruthenium (III) 3-sulphate were respectively 12 times and 9.5 times higher than those in Comparative Examples. In this way, it was confirmed that these compounds have extremely high catalytic activities.

The turnover numbers of the catalysts in Examples were 4.8 to 12 times higher than those in Comparative Examples. In this way, it was confirmed that the catalysts used in Examples have much higher turnover numbers and hence are excellent as catalysts. Particularly, turnover numbers of ruthenium trichloride and di[triaqua {2.6-di(phenylthiomethyl) pyridine} ruthenium (III) 3-sulphate are respectively 12 times and 9.5 times higher than those in Comparative Examples. In this way, it was confirmed that the compounds are extremely excellent as a catalyst.

Further, comparison between the results of Examples 5 to 8 and the results of Comparative Example 2, comparison between the results of Examples 9 to 11 and the results of Comparative Example 3, and comparison between the results of Examples 12 to 15 and the results of Comparative Example 4 show that the results of Examples were favorable and hence the method according to the present invention for synthesis of keto acids is excellent.

Example 21

0.1 mmol of water-soluble acetylene carboxylic acids whose R$^1$ and R$^2$ are H in FIG. 1(a) was mixed with 2 mL of aqueous solution containing 1.0 μmol of ruthenium trichloride, and the mixture was reacted at the pH 1.3 at 100° C. under argon atmosphere for 12 hours. The resulting reaction mixture was condensed to give a product. The product was analyzed by $^1$H NMR.

Example 22

0.1 mmol of water-soluble acetylene carboxylic acids whose R$^1$ and R$^2$ are H in FIG. 1(a) was mixed with 2 mL of aqueous solution containing 1.0 μmol of rhodium trichloride, and the mixture was reacted at the pH 1.3 at 100° C. under argon atmosphere for 12 hours. The resulting reaction mixture was condensed to give a product. The product was analyzed by $^1$H NMR.

Example 23

0.1 mmol of water-soluble acetylene carboxylic acids whose R$^1$ and R$^2$ are H in FIG. 1(a) was mixed with 2 mL of aqueous solution containing 1.0 μmol of iridium trichloride, and the mixture was reacted at the pH 1.3 at 100° C. under argon atmosphere for 12 hours. The resulting reaction mixture was condensed to give a product. The product was analyzed by $^1$H NMR.

Comparative Example 5

The same operation as in Examples 21 to 23 except that HgSO$_4$ was used as a catalyst.

Example 24

0.1 mmol of water-soluble acetylene dicarboxylic acids whose R$^1$ is CH$_3$ and R$^2$ is H in FIG. 1(a) was mixed with 2 mL of aqueous solution containing 1.0 μmol of ruthenium trichloride, and the mixture was reacted at the pH 1.3 at 100° C. under argon atmosphere for 24 hours. The resulting reaction mixture was condensed to give a product. The product was analyzed by $^1$H NMR.

Example 25

0.1 mmol of water-soluble acetylene dicarboxylic acids whose R$^1$ is CH$_3$ and R$^2$ is H in FIG. 1(a) was mixed with 2 mL of aqueous solution containing 1.0 μmol of rhodium trichloride, and the mixture was reacted at the pH 1.3 at 100° C. under argon atmosphere for 24 hours. The resulting reaction mixture was condensed to give a product. The product was analyzed by $^1$H NMR.

Example 26

0.1 mmol of water-soluble acetylene dicarboxylic acids whose R$^1$ is CH$_3$ and R$^2$ is H in FIG. 1(a) was mixed with 2 mL of aqueous solution containing 1.0 μmol of iridium trichloride, and the mixture was reacted at the pH 1.3 at 100° C. under argon atmosphere for 24 hours. The resulting reaction mixture was condensed to give a product. The product was analyzed by $^1$H NMR.

Comparative Example 6

The same operation as in Examples 24 to 26 except that HgSO$_4$ was used as a catalyst.

Example 27

0.1 mmol of water-soluble acetylene dicarboxylic acids whose R$^1$ is C$_6$H$_5$ and R$^2$ is H in FIG. 1(a) was mixed with 2 mL of aqueous solution containing 1.0 μmol of ruthenium trichloride, and the mixture was reacted at the pH 4.5 at 100° C. under argon atmosphere for 24 hours. The resulting reaction mixture was condensed to give a product. The product was analyzed by $^1$H NMR.

Comparative Example 7

The same operation as in Example 27 except that $HgSO_4$ was used as a catalyst.

Example 28

0.1 mmol of water-soluble acetylene dicarboxylic acids whose $R^1$ is COOH and $R^2$ is H in FIG. 1(a) was mixed with 2 mL of aqueous solution containing 1.0 μmol of ruthenium trichloride, and the mixture was reacted at the pH 1.3 at 100° C. under argon atmosphere for 12 hours. The resulting reaction mixture was condensed to give a product. The product was analyzed by $^1$H NMR.

Example 29

0.1 mmol of water-soluble acetylene dicarboxylic acids whose $R^1$ is $C_3H_7$ and $R^2$ is H in FIG. 1(a) was mixed with 2 mL of aqueous solution containing 1.0 μmol of ruthenium trichloride, and the mixture was reacted at the pH 3.5 at 100° C. under argon atmosphere for 12 hours. The resulting reaction mixture was condensed to give a product. The product was analyzed by $^1$H NMR.

[Results of Examples 21 to 29 and Comparative Examples 5 to 7]

Table 2 shows the results. See Table 2 in the same manner as in Table 1.

TABLE 2

|  | $R^1$ | $R^2$ |  | Cat | Path | TON | mol % | Yield (%) |
|---|---|---|---|---|---|---|---|---|
| Example 21 | H | H | water-soluble | $RuCl_3$ | A | 90 | 1 | 90 |
| Example 22 | H | H | water-soluble | $RhCl_3$ | A | 19 | 1 | 19 |
| Example 23 | H | H | water-soluble | $IrCl_3$ | A | 29 | 1 | 29 |
| Comparative Example 5 | H | H | water-soluble | $HgSO_4$ | A | 7 | 1 | 7 |
| Example 24 | $CH_3$ | H | water-soluble | $RuCl_3$ | A | 51 | 1 | 51 |
| Example 25 | $CH_3$ | H | water-soluble | $RhCl_3$ | A | 8 | 1 | 8 |
| Example 26 | $CH_3$ | H | water-soluble | $IrCl_3$ | A | 2 | 1 | 2 |
| Comparative Example 6 | $CH_3$ | H | water-soluble | $HgSO_4$ | A | — | 1 | — |
| Example 27 | $C_6H_5$ | H | water-soluble | $RuCl_3$ | A | 15 | 1 | 15 |
| Comparative Example 7 | $C_6H_5$ | $C_2H_5$ | water-soluble | $HgSO_4$ | A | — | 1 | — |
| Example 28 | COOH | $C_2H_5$ | water-soluble | $RuCl_3$ | A | 64 | 1 | 64 |
| Example 29 | $C_3H_7$ | $C_2H_5$ | water-soluble | $RuCl_3$ | A | 24 | 1 | 24 |

The yields and turnover numbers of the keto acids of Examples 21 to 23 were 2.7 to 13 times higher than that in Comparative Example 5 using mercury sulfate. In this way, it was confirmed that the catalysts (ruthenium trichloride, rhodium trichloride, and iridium trichloride) used in Examples have much higher catalytic activities than that of mercury sulfate. Particularly, the yield and turnover number in using ruthenium trichloride as a catalyst was 13 times higher than that in Comparative Example 5. In this way, it was confirmed that ruthenium trichloride is a particularly excellent catalyst in the reactions of Examples.

Comparative Example 6 using mercury sulfate resulted in formation of no keto acids, but Examples 24 to 26 resulted in formation of keto acids. Thus, it was confirmed that the catalysts (ruthenium trichloride, rhodium trichloride, and iridium trichloride) used in Examples are much more excellent than mercury sulfate. Particularly, in Example 24 using ruthenium trichloride, keto acids were formed at such an extremely high yield as 51%. In this way, it was confirmed that ruthenium trichloride is a particularly excellent catalyst in the reactions of Examples.

Comparative Example 7 using mercury sulfate resulted in formation of no keto acids, but Example 27 resulted in formation of keto acids. Thus, it was confirmed that the catalyst (ruthenium trichloride) used in Example 27 is much more excellent as a catalyst than mercury sulfate.

Also Examples 28 and 29 resulted in formation of keto acids.

Note that, Examples 21 and Example 1 are different only in a reaction temperature, i.e., whether the reaction temperature is 100° C. or 80° C. Comparison between Example 21 and Example 1 in the keto-acid yield and turnover number shows that the keto-acid yield and turnover number are increased by changing the reaction temperature from 80° C. to 100° C. On the other hand, Example 24 and Example 9 were different from each other not only in the reaction temperature (100° C. or 80° C.) but also in a ratio of acetylene-carboxylic acids and catalyst. However, although the catalyst ratio was 1/5, the keto-acid yield and turnover number in Example 24 was about 1.5 times higher than those in Example 9. Note that, each of the catalysts used in Examples 1, 21, 24, and 9 was ruthenium trichloride. This shows that 100° C. is more preferable than 80° C. as the reaction temperature in the hydration of acetylene-carboxylic acids with ruthenium trichloride used as a catalyst.

Example 30

0.1 mmol of water-insoluble acetylene dicarboxylate ester whose $R^1$ is H and $R^2$ is $C_2H_5$ in FIG. 1(b) was mixed with 2 mL of acetic acid buffer aqueous solution containing 1.0 μmol of ruthenium trichloride, and the mixture was reacted at the pH 4.0 at 80° C. under argon atmosphere for 12 hours. The resulting reaction mixture was extracted and condensed with chloroform to give a product. The product was analyzed by $^1$H NMR.

Example 31

0.1 mmol of water-insoluble acetylene dicarboxylate ester whose $R^1$ is H and $R_2$ is $C_2H_5$ in FIG. 1(b) was mixed with 2 mL of acetic acid buffer aqueous solution containing 1.0 μmol of rhodium trichloride, and the mixture was reacted at the pH 4.0 at 80° C. under argon atmosphere for 12 hours. The resulting reaction mixture was extracted and condensed with chloroform to give a product. The product was analyzed by $^1$H NMR.

Example 32

0.1 mmol of water-insoluble acetylene dicarboxylate ester whose $R^1$ is H and $R^2$ is $C_2H_5$ in FIG. 1(b) was mixed with 2 mL of acetic acid buffer aqueous solution containing 1.0 μmol of iridium trichloride, and the mixture was reacted at the pH 4.0 at 80° C. under argon atmosphere for 12 hours. The resulting reaction mixture was extracted and condensed with chloroform to give a product. The product was analyzed by $^1$H NMR.

Comparative Example 8

The same operation as in Examples 30 to 32 except that $HgSO_4$ was used as a catalyst.

Example 33

0.1 mmol of water-insoluble acetylene dicarboxylate ester whose $R^1$ is $CH_3$ and $R_2$ is $C_2H_5$ in FIG. 1(b) was mixed with 2 mL of acetic acid buffer aqueous solution containing 1.0 μmol of rhodium trichloride, and the mixture was reacted at the pH 4.0 at 80° C. under argon atmosphere for 12 hours. The resulting reaction mixture was extracted and condensed with chloroform to give a product. The product was analyzed by $^1$H NMR.

Example 34

0.1 mmol of water-insoluble acetylene dicarboxylate ester whose $R^1$ is $CH_3$ and $R_2$ is $C_2H_5$ in FIG. 1(b) was mixed with 2 mL of acetic acid buffer aqueous solution containing 1.0 μmol of iridium trichloride, and the mixture was reacted at the pH 4.0 at 80° C. under argon atmosphere for 12 hours. The resulting reaction mixture was extracted and condensed with chloroform to give a product. The product was analyzed by $^1$H NMR.

Comparative Example 9

The same operation as in Examples 33 to 34 except that $HgSO_4$ was used as a catalyst.

Example 35

0.1 mmol of water-insoluble acetylene dicarboxylate ester whose $R^1$ is $C_4H_9$ and $R_2$ is $C_2H_5$ in FIG. 1(b) was mixed with 2 mL of acetic acid buffer aqueous solution containing 10 μmol of rhodium trichloride, and the mixture was reacted at the pH 4.0 at 80° C. under argon atmosphere for 12 hours. The resulting reaction mixture was extracted and condensed with chloroform to give a product. The product was analyzed by $^1$H NMR.

Example 36

0.1 mmol of water-insoluble acetylene dicarboxylate ester whose $R^1$ is $C_4H_9$ and $R_2$ is $C_2H_5$ in FIG. 1(b) was mixed with 2 mL of acetic acid buffer aqueous solution containing 10 μmol of iridium trichloride, and the mixture was reacted at the pH 4.0 at 80° C. under argon atmosphere for 12 hours. The resulting reaction mixture was extracted and condensed with chloroform to give a product. The product was analyzed by $^1$H NMR.

Comparative Example 10

The same operation as in Examples 35 to 36 except that $HgSO_4$ was used as a catalyst.

[Results of Examples 30 to 36 and Comparative Examples 8 to 10]

Table 3 shows the results. See Table 3 in the same manner as in Table 1.

TABLE 3

| | $R^1$ | $R^2$ | | Cat | Path | TON | mol % | Yield (%) |
|---|---|---|---|---|---|---|---|---|
| Example 30 | H | $C_2H_5$ | water-insoluble | $RuCl_3$ | C | 3.4 | 1 | 3.4 |
| Example 31 | H | $C_2H_5$ | water-insoluble | $RhCl_3$ | C | 2.3 | 1 | 2.3 |
| Example 32 | H | $C_2H_5$ | water-insoluble | $IrCl_3$ | C | 4.9 | 1 | 4.9 |
| Comparative Example 8 | H | $C_2H_5$ | water-insoluble | $HgSO_4$ | C | 2.0 | 1 | 2.0 |
| Example 33 | $CH_3$ | $C_2H_5$ | water-insoluble | $RhCl_3$ | C | 12 | 1 | 12 |
| Example 34 | $CH_3$ | $C_2H_5$ | water-insoluble | $IrCl_3$ | C | 71 | 1 | 71 |
| Comparative Example 9 | $CH_3$ | $C_2H_5$ | water-insoluble | $HgSO_4$ | C | 7 | 1 | 7 |
| Example 35 | $C_4H_9$ | $C_2H_5$ | water-insoluble | $RhCl_3$ | C | 1.1 | 10 | 11 |
| Example 36 | $C_4H_9$ | $C_2H_5$ | water-insoluble | $IrCl_3$ | C | 2.1 | 10 | 21 |
| Comparative Example 10 | $C_4H_9$ | $C_2H_5$ | water-insoluble | $HgSO_4$ | C | 1.2 | 10 | 12 |

The keto-acid ester yields and turnover numbers in Examples 30 to 32 were equal to or higher than that in Comparative Example 8 using mercury sulfate. This shows that the present invention allows for synthesis of keto acids by hydration of an acetylene compound under mild conditions free from any harmful mercury catalysts.

The keto-acid ester yields and turnover numbers in Examples 33 to 34 were higher than Comparative Example 9 using mercury sulfate. This shows that the catalysts (ruthenium trichloride, rhodium trichloride, and iridium trichloride) used in Examples are much more excellent than mercury sulfate. Particularly, in Example 34 using rhodium trichloride, keto acids were formed at such an extremely high yield as 71%. In this way, it was confirmed that rhodium trichloride is a particularly excellent catalyst in the reactions of Examples.

The keto-acid ester yields and turnover numbers in Examples 35 to 36 were equal to or higher than Comparative Example 10 using mercury sulfate. This shows that the present invention allows for synthesis of keto acids by hydration of an acetylene compound under mild conditions free from any harmful mercury catalyst.

<2. Synthesis of Amino Acid and Amino Acid Derivative>

Figure 2A:
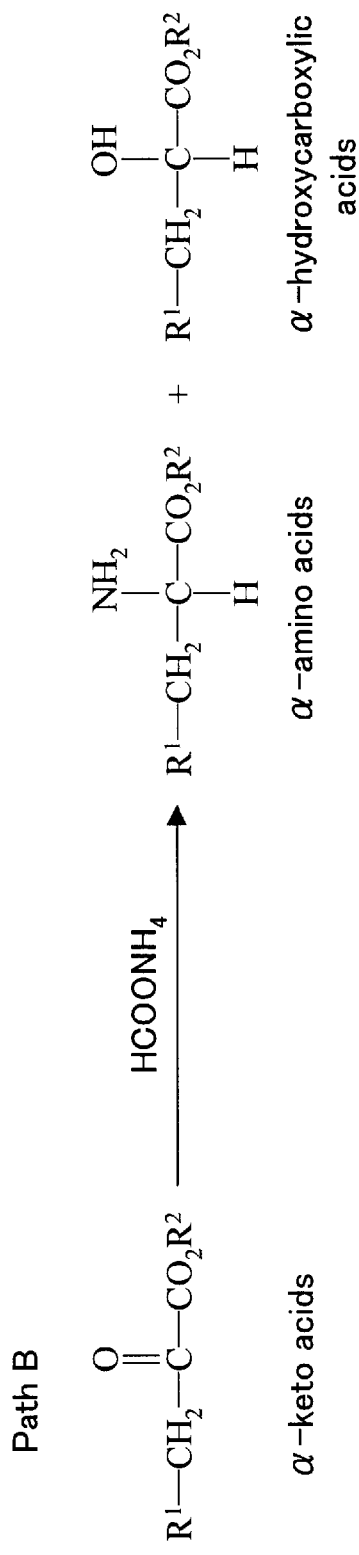
FIG. 2(a) is a drawing illustrating a reaction formula of synthesis amino acids (including amino acid and amino acid derivative) by reductive amination of α-keto acids (including α-keto acid and α-keto acid derivative) in the presence of a transmission metal complex in Referential Example.
Figure 2B:
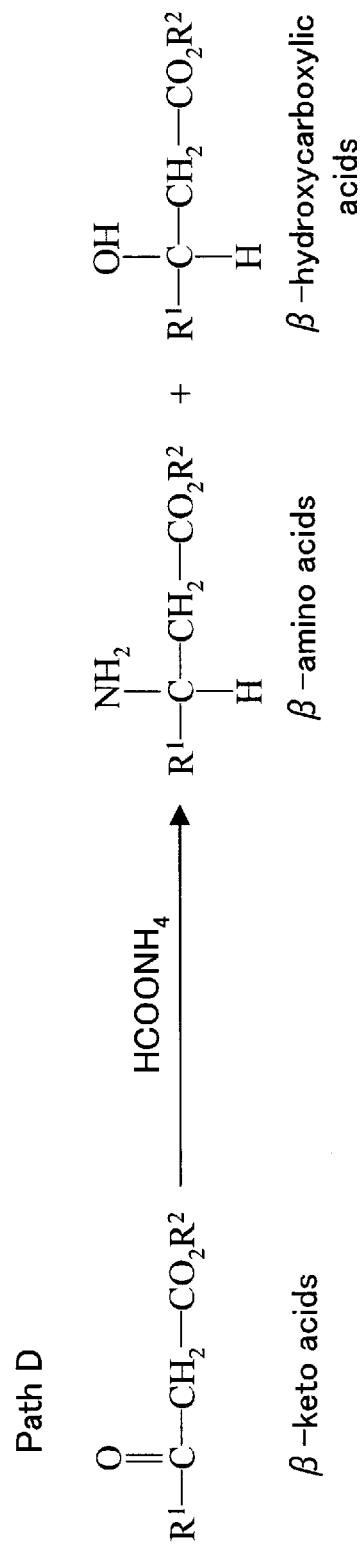
FIG. 2(b) is a drawing illustrating a reaction formula of synthesis amino acids (including amino acid and amino acid derivative) by reductive amination of β-keto acids (including β-keto acid and β-keto acid derivative) in the presence of a transmission metal complexe in Referential Example.

Reductive amination of keto acids was performed in the presence of a transition metal complex to synthesize amino acids. Each of FIG. 2(a) and FIG. 2(b) shows a reaction formula of the reductive amination. Note that, when reductive amination of α-keto acids was performed, α-amino acids and α-hydroxy-carboxylic acids were synthesized (FIG. 2(a)), and when reductive amination of β-keto acids was performed, β-amino acids and β-hydroxy-carboxylic acids were synthesized (FIG. 2(b)). For convenience in descriptions, a reaction path shown in FIG. 2(a) is referred to as "Path B" and a reaction path shown in FIG. 2(b) is referred to as "Path D".

Referential Example 1

0.16 mmol of pyruvic acid whose $R^1$ is $CH_3$ and $R^2$ is H in FIG. 2(a) and 3.2 mmol of formate ammonium were poured into 3 mL of water so as to have the pH 4.5. 0.2 μmol of ($\eta^5$-tetramethylcyclopentadienyl) rhodium (III) (2,2'-bipyridyl) aqua complex was added to the pyruvic acid aqueous solution, and the resulting mixture was reacted at 80° C. under argon atmosphere for an hour. After completion of the reaction, the resulting product was analyzed by $^1$H NMR. In isolation of the product, the reaction solution was condensed, and the condensed residue was dissolved in water, and the resulting water was made to pass through a cation exchange resin (DOWEX 50W-X2). After flowing 50 mL of water, 200 mL of 0.1 M aqueous ammonia was flown, and the solution was condensed to give a product (alanine).

Referential Example 2

0.16 mmol of 4-hydroxy pyruvic acid whose $R^1$ is $C_6H_4$(OH) and $R^2$ is H in FIG. 2(a) and 3.2 mmol of formate ammonium were poured into 3 mL of water so as to have the pH 4.5. 0.2 μmol of ($\eta^5$-tetramethylcyclopentadienyl) rhodium (III)(2,2'-bipyridyl) aqua complex was added to the pyruvic acid aqueous solution, and the resulting mixture was reacted at 80° C. under argon atmosphere for an hour. After completion of the reaction, the resulting product was analyzed by $^1$H NMR. In isolation of the product, the reaction mixture was filtrated to give tyrosine, i.e., a reaction product.

Referential Example 3

0.16 mmol of keto glutaric acid whose $R^1$ is $(CH_2)_2COOH$ and $R^2$ is H in FIG. 2(a) and 3.2 mmol of formate ammonium were poured into 3 mL of water so as to have the pH 4.5. 0.2 μmol of ($\eta^5$-tetramethylcyclopentadienyl) rhodium (III)(2,2'-bipyridyl) aqua complex was added to the pyruvic acid aqueous solution, and the resulting mixture was reacted at 80° C. under argon atmosphere for an hour. After completion of the reaction, the resulting product was analyzed by $^1$H NMR. In isolation of the product, the reaction solution was condensed, and the condensed residue was dissolved in water, and the resulting water was made to pass through a cation exchange resin (DOWEX 50W-X2). After flowing 50 mL of water, 200 mL of 0.1M aqueous ammonia was flown, and the solution was condensed to give glutamic acid.

Referential Example 4

3.2 mmol of formate acid ammonium was poured into 3 mL of water so as to have the pH 4.5. 0.2 mmol of ($\eta^5$-tetramethylcyclopentadienyl) rhodium (III) (2,2'-bipyridyl) aqua complex and 0.2 μmol of ethyl acetoacetate whose $R^1$ is $CH_3$ and $R^2$ is $C_2H_5$ in FIG. 2(b) were poured into the prepared formate ammonium aqueous solution, and the resulting mixture was reacted at 80° C. under argon atmosphere for an hour. After completion of the reaction, the pH of the reaction solution was adjusted to 9.0. Thereafter, extraction and condensation were performed with dichloromethane or diethyl ether to give a product. The resulting product was analyzed by $^1$H NMR. In isolation of the product, the reaction solution was condensed, and the condensed residue was dissolved in water, and the resulting water was made to pass through a cation exchange resin (DOWEX 50W-X2). After flowing 50 mL of water, 200 mL of 0.1M aqueous ammonia was flown, and the solution was condensed to give 3-aminobutanate ethyl.

[Results of Referential Examples 1 to 4]

TABLE 4

| | $R^1$ | $R^2$ | | Cat | Path | TON | mol % | Yield (%) |
|---|---|---|---|---|---|---|---|---|
| Referential Example 1 | $CH_3$ | H | water-soluble | Cp*Rh$^{III}$(bpy)(OH$_2$) | B | 750 | 0.13 | 94 |
| Referential Example 2 | $C_6H_4$(OH) | H | water-soluble | Cp*Rh$^{III}$(bpy)(OH$_2$) | B | 350 | 0.13 | 44 |
| Referential Example 3 | $(CH_2)_2COOH$ | H | water-soluble | Cp*Rh$^{III}$(bpy)(OH$_2$) | B | 300 | 0.13 | 38 |
| Referential Example 4 | $CH_3$ | $C_2H_5$ | water-insoluble | Cp*Rh$^{III}$(bpy)(OH$_2$) | D | 70 | 1 | 70 |

In Table 4, "mol %" represents mol % of each catalyst with respect to the keto acids, and "Yield (%)" represents an yield of amino acids produced from the keto acids. Other items are the same as in Table 1.

Table 4 shows that amino acids can be efficiently synthesized by reductive amination of keto acids in the presence of a transition metal complex (($\eta^5$-tetramethylcyclopentadienyl) rhodium (III)(2,2'-bipyridyl) aqua complex). Also, Table 4 shows that amino acids can be synthesized regardless of whether the keto acids are water-soluble keto acids (Referential Examples 1 to 3) or water-insoluble keto-acid ester (Referential Example 4).

Further, the turnover number of the catalyst was high, which shows that the method in Referential Examples is extremely excellent. Particularly in case of Referential Example 1, the resulting amino acids were formed at such an extremely high yield as 94%. In this way, the method is excellent in selectivity with respect to synthesis of amino acids.

<3. Method for One-Pot Synthesis of Amino Acids From Acetylene-Carboxylic Acids>

Synthesis of keto acids by the hydration and synthesis of amino acids by reductive amination of the keto acids were sequentially performed to carry out one-pot synthesis of amino acids from acetylene-carboxylic acids. Each of FIG. 3(a) and FIG. 3(b) shows a reaction formula of the reaction. Note that, when water-soluble acetylene-carboxylic acids were used as starting material, α-keto acids were synthesized to finally give α-amino acids (FIG. 3(a)), and when water-insoluble acetylene-carboxylic acids were used as starting material, β-keto acids were synthesized to finally give β-amino acids (FIG. 3(b)).

Example 16

5 mmol of water-soluble acetylene-carboxylic acids whose $R^1$ and $R^2$ are H in FIG. 3 was poured into 10 mL of water so as to have the pH 2.0. 5.0 μmol of rhodium chloride was added to the solution, and the resulting mixture was reacted at 80° C. under argon atmosphere. After 36 hours, 10 mmol of formate ammonium and 5.0 μmol of aqua($\eta^5$-tetramethylcyclopentadienyl) rhodium (III)(2,2'-bipyridyl) sulphate were added, and the resulting mixture was further reacted for two hours. After completion of the reaction, the resulting product was analyzed by $^1$H NMR.

Example 17

5 mmol of water-soluble acetylene-carboxylic acids whose $R^1$ and $R^2$ are H in FIG. 3 was poured into 10 mL of water so as to have the pH 2.0. 5.0 μmol of ruthenium chloride was added to the solution, and the resulting mixture was reacted at 80° C. under argon atmosphere. After 36 hours, 10 mmol of formate ammonium and 5.0 μmol of aqua($\eta^5$-tetramethylcyclopentadienyl) rhodium (III)(2,2'-bipyridyl) sulphate were added, and the resulting mixture was further reacted for two hours. After completion of the reaction, the resulting product was analyzed by $^1$H NMR.

Example 18

5 mmol of water-soluble acetylene-carboxylic acids whose $R^1$ is $CH_3$ and $R^2$ is H in FIG. 3 was poured into 10 mL of water so as to have the pH 2.0. 5.0 μmol of ruthenium chloride was added to the solution, and the resulting mixture was reacted at 80° C. under argon atmosphere. After 36 hours, 10 mmol of formate ammonium and 5.0 μmol of aqua($\eta^5$-tetramethylcyclopentadienyl) rhodium (III)(2,2'-bipyridyl) sulphate were added, and the resulting mixture was further reacted for two hours. After completion of the reaction, the resulting product was analyzed by $^1$H NMR.

Example 19

5 mmol of water-soluble acetylene-carboxylic acids whose $R^1$ is $CH_3$ and $R^2$ is H in FIG. 3 was poured into 10 mL of water so as to have the pH 2.0. 5.0 μmol of ruthenium chloride was added to the solution, and the resulting mixture was reacted at 80° C. under argon atmosphere. After 36 hours, 10 mmol of formate ammonium and 5.0 μmol of ($\eta^5$-tetramethylcyclopentadienyl) rhodium (III) (2,2'-bipyridyl) aqua complex were added, and the resulting mixture was further reacted for two hours. After completion of the reaction, the resulting product was analyzed by $^1$H NMR.

Example 20

0.1 mmol of water-insoluble acetylene-dicarboxylic acids whose $R^1$ is $CH_3$ and $R^2$ is $C_2H_5$ in FIG. 3 was poured into 10 mL of water so as to have the pH 2.0. 5.0 μmol of rhodium chloride was added to the solution, and the resulting mixture was reacted at 80° C. under argon atmosphere. After 12 hours, 10 mmol of formate ammonium and 1.0 μmol of ($\eta^5$-tetramethylcyclopentadienyl) rhodium (III) (2,2'-bipyridyl) aqua complex were added, and the resulting mixture was further reacted for two hours. After completion of the reaction, the resulting product was analyzed by $^1$H NMR.

[Results of Examples 16 to 20]

Table 5 shows the results.

TABLE 5

| | $R^1$ | $R^2$ | | hydration | reductive amination | Path | TON | Yield (%) |
|---|---|---|---|---|---|---|---|---|
| | | | | Cat(mol %) | | | | |
| Example 16 | H | H | water-soluble | $RhCl_3$ 0.1 | $Cp^*Rh^{III}(bpy)(OH_2)$ 0.1 | A + B | 130 | 13 |
| Example 17 | H | H | water-soluble | $RuCl_3$ 0.1 | $Cp^*Rh^{III}(bpy)(OH_2)$ 0.1 | A + B | 280 | 28 |
| Example 18 | $CH_3$ | H | water-soluble | $RuCl_3$ 0.1 | $Cp^*Rh^{III}(bpy)(OH_2)$ 0.1 | A + B | 110 | 11 |
| Example 19 | $CH_3$ | H | water-soluble | $RuCl_3$ 0.1 | $Cp^*Rh^{III}(bpy)(OH_2)$ 0.1 | A + B | 10 | 1 |
| Example 20 | $CH_3$ | $C_2H_5$ | water-insoluble | $RhCl_3$ 5 | $Cp^*Rh^{III}(bpy)(OH_2)$ 1 | C + D | 7 | 35 |

In Table 5, a numerical value indicated below each catalyst in "Cat (mol %)" represents mol % of the catalyst with respect to acetylene-carboxylic acids, and "Yield (%)" represents an yield of amino acids synthesized from acetylene-carboxylic acids. Other items are the same as in Table 1.

Table 5 shows that one-pot synthesis of amino acids can be performed by using any one of the water-soluble substances (Examples 16 to 19) and the water-insoluble substance (Example 20).

Example 37

0.1 mmol of water-soluble acetylene-carboxylic acids whose $R^1$ and $R^2$ are H in FIG. 3 was poured into 2 mL of water so as to have the pH 1.3. 1.0 μmol of ruthenium chloride was added to the solution, and the resulting mixture was reacted at 100° C. under argon atmosphere. After 12 hours, 4 mmol of formate ammonium and 1.0 μmol of aqua($\eta^5$-tetramethylcyclopentadienyl) rhodium (III)(2,2'-bipyridyl) sulphate were added, and the resulting mixture was further reacted at 80° C. for an hour. After completion of the reaction, the resulting product was analyzed by $^1$H NMR.

Example 38

0.1 mmol of water-soluble acetylene-carboxylic acids whose $R^1$ and $R^2$ are H in FIG. 3 was poured into 2 mL of water so as to have the pH 1.3. 1.0 μmol of ruthenium chloride was added to the solution, and the resulting mixture was reacted at 100° C. under argon atmosphere. After 12 hours, 4 mmol of formate ammonium and 0.1 μmol of aqua($\eta^5$-tetramethylcyclopentadienyl) rhodium (III)(2,2'-bipyridyl) sulphate were added, and the resulting mixture was further reacted at 80° C. for an hour. After completion of the reaction, the resulting product was analyzed by $^1$H NMR.

Example 39

0.1 mmol of water-soluble acetylene-carboxylic acids whose $R^1$ and $R^2$ are H in FIG. 3 was poured into 2 mL of water so as to have the pH 1.3. 1.0 µmol of ruthenium chloride was added to the solution, and the resulting mixture was reacted at 100° C. under argon atmosphere. After 12 hours, 4 mmol of formate ammonium and 1.0 µmol of aqua($\eta^5$-tetramethylcyclopentadienyl) iridium (III)(2,2'-bipyridyl) sulfate were added, and the resulting mixture was further reacted at 80° C. for one hour. After completion of the reaction, the resulting product was analyzed by $^1$H NMR.

Example 40

0.1 mmol of water-soluble acetylene-carboxylic acids whose $R^1$ is $CH_3$ and $R^2$ is H in FIG. 3 was poured into 2 mL of water so as to have the pH 1.3. 1.0 µmol of ruthenium chloride was added to the solution, and the resulting mixture was reacted at 100° C. under argon atmosphere. After 12 hours, 4 mmol of formate ammonium and 1.0 µmol of aqua ($\eta^5$-tetramethylcyclopentadienyl) rhodium (III)(2,2'-bipyridyl) sulphate were added, and the resulting mixture was further reacted at 80° C. for an hour. After completion of the reaction, the resulting product was analyzed by $^1$H NMR.

Example 41

0.1 mmol of water-soluble acetylene-carboxylic acids whose $R^1$ is $CH_3$ and $R^2$ is H in FIG. 3 was poured into 2 mL of water so as to have the pH 1.3. 1.0 µmol of ruthenium chloride was added to the solution, and the resulting mixture was reacted at 100° C. under argon atmosphere. After 12 hours, 4 mmol of formate ammonium and 1.0 µmol of aqua ($\eta^5$-tetramethylcyclopentadienyl) iridium (III)(2,2'-bipyridyl) sulphate were added, and the resulting mixture was further reacted at 80° C. for an hour. After completion of the reaction, the resulting product was analyzed by $^1$H NMR.

Example 42

0.1 mmol of water-insoluble acetylene-carboxylic acids whose $R^1$ is $CH_3$ and $R^2$ is $C_2H_5$ in FIG. 3 was poured into 2 mL of water so as to have the pH 4.0. 1.0 µmol of iridium chloride was added to the solution, and the resulting mixture was reacted at 80° C. under argon atmosphere. After 24 hours, 4 mmol of formate ammonium and 1.0 µmol of aqua($\eta^5$-tetramethylcyclopentadienyl) rhodium (III)(2,2'-bipyridyl) sulphate were added, and the resulting mixture was further reacted at 80° C. for an hour. After completion of the reaction, the resulting product was analyzed by $^1$H NMR.

Example 43

0.1 mmol of water-insoluble acetylene-carboxylic acids whose $R^1$ is $CH_3$ and $R^2$ is $C_2H_5$ in FIG. 3 was poured into 2 mL of water so as to have the pH 4.0. 1.0 µmol of iridium chloride was added to the solution, and the resulting mixture was reacted at 80° C. under argon atmosphere. After 24 hours, 4 mmol of formate ammonium and 1.0 µmol of aqua($\eta^5$-tetramethylcyclopentadienyl) iridium (III) (2,2'-bipyridyl) sulphate were added, and the resulting mixture was further reacted at 80° C. for an hour. After completion of the reaction, the resulting product was analyzed by $^1$H NMR.

[Results of Examples 37 to 43]

Table 6 shows the results. See Table 6 in the same manner as in Table 5.

TABLE 6

| | $R^1$ | $R^2$ | | Cat (mol %) hydration | reductive amination | Path | TON | Yield (%) |
|---|---|---|---|---|---|---|---|---|
| Example 37 | H | H | water-soluble | $RuCl_3$ 1 | Cp*Rh$^{III}$(bpy)(OH$_2$) 1 | A + B | 77 | 77 |
| Example 38 | H | H | water-soluble | $RuCl_3$ 1 | Cp*Rh$^{III}$(bpy)(OH$_2$) 1 | A + B | 60 | 60 |
| Example 39 | H | H | water-soluble | $RuCl_3$ 1 | Cp*Ir$^{III}$(bpy)(OH$_2$) 1 | A + B | 80 | 80 |
| Example 40 | $CH_3$ | H | water-soluble | $RuCl_3$ 1 | Cp*Rh$^{III}$(bpy)(OH$_2$) 1 | A + B | 40 | 40 |
| Example 41 | $CH_3$ | H | water-soluble | $RuCl_3$ 1 | Cp*Ir$^{III}$(bpy)(OH$_2$) 1 | A + B | 36 | 36 |
| Example 42 | $CH_3$ | $C_2H_5$ | water-insoluble | $IrCl_3$ 1 | Cp*Rh$^{III}$(bpy)(OH$_2$) 1 | C + D | 12 | 12 |
| Example 43 | $CH_3$ | $C_2H_5$ | water-insoluble | $IrCl_3$ 1 | Cp*Ir$^{III}$(bpy)(OH$_2$) 1 | C + D | 4.3 | 4.3 |

Table 6 shows that one-pot synthesis of amino acids can be performed by using any one of the water-soluble substances (Examples 37 to 41) and the water-insoluble substances (Examples 42 to 43). Particularly in case of Examples 37, 38, and 39, the amino-acid yields (%) and turnover numbers are respectively 77, 60, and 80. These are extremely favorable results.

INDUSTRIAL APPLICABILITY

According to the present invention, keto acids can be easily synthesized from acetyl-carboxylic acids. Further, amino acids can be easily synthesized from the keto acids. Moreover, amino acids can be sequentially synthesized from acetyl-carboxylic acids in a single container. The amino acids are extremely significant in living organisms such as a human.

Therefore, the present invention is applicable to an industry producing amino acids, e.g., a pharmaceutical industry, a research reagent industry, and a food industry, in particular.

The invention claimed is:

1. A method for synthesis of keto acids, comprising the step of hydrating acetylene-carboxylic acids in the presence of a metal salt represented by General Formula (1), General Formula (1)

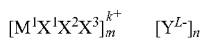

where $M^1$ represents Ru, Rh or Ir, and $X^1$, $X^2$, and $X^3$ ligand represents halogen, $H_2O$, or a solvent molecule, and k represents a valence of a cation species, and Y represents an anion species, and L represents a valence of the anion species, and each of K and L independently represents 1 or 2, and k×m=L×n.

2. The method as set forth in claim 1, wherein the hydration is performed in the presence of an organic solvent which is inert in reaction.

3. The method set forth in claim 1, comprising the step of hydrating acetylene-carboxylic acids in the presence of the metal salt represented by General Formula (1), and at least one selected from a group consisting of a transition metal complex represented by General Formula (2), a transition metal complex represented by General Formula (3), and a transition metal complex represented by General Formula (8), General Formula (1)

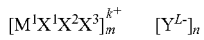

where $M^1$ represents Ru, Rh or Ir, and $X^1$, $X^2$, and $X^3$ ligand represents halogen, $H_2O$, or a solvent molecule, and k represents a valence of a cation species, and Y represents an anion species, and L represents a valence of the anion species, and each of K and L independently represents 1 or 2, and k×m=L×n, General Formula (2)

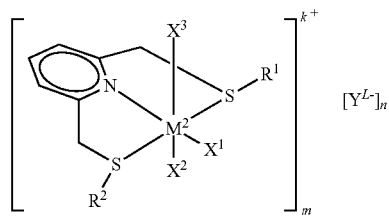

where each of $R^1$ and $R^2$ independently represents a hydrogen atom or a $C_1$ to $C_6$ lower alkyl group, and $M^2$ represents Ru or Rh, and $X^1$ and $X^2$ ligand represents $H_2O$, halogen, a solvent molecule, or nitrous ligand, and $X^3$ ligand represents halogen, $H_2O$, or a solvent molecule, and k represents a valence of a cation species, and Y represents an anion species, and L represents a valence of the anion species, and each of K and L independently represents 1 or 2, and k×m=L×n, General Formula (3)

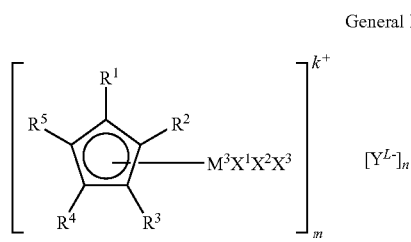

where each of $R^1$, $R^2$, $R^3$, $R^4$, and $R^5$ independently represents a hydrogen atom or a $C_1$ to $C_6$ lower alkyl group, and $M^3$ represents Ru, Rh or Ir, and each of $X^1$ and $X^2$ represents nitrous ligand, and $X^3$ represents a hydrogen atom, a carboxylic acid residue, or $H_2O$, and $X^1$ and $X^2$ may be bonded to each other, and k represents a valence of a cation species, and Y represents an anion species, and L represents a valence of the anion species, and each of K and L independently represents 1 or 2, and k×m=L×n, General Formula (8)

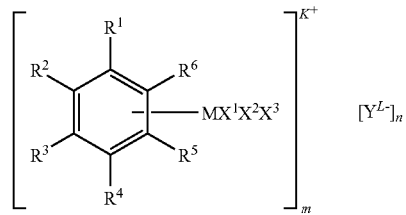

where each of $R^1$, $R^2$, $R^3$, $R^4$, $R^5$ and $R^6$ independently represents a hydrogen atom or a $C_1$ to $C_6$ lower alkyl group, and M represents Ru, and each of $X^1$, $X^2$ and $X^3$ represents halogen, $H_2O$, or a solvent molecule, and k represents a valence of a cation species, and Y represents an anion species, and L represents a valence of the anion species, and each of K and L independently represents 1 or 2, and k×m=L×n.

4. The method as set forth in claim 3, wherein the hydration is performed in the presence of an organic solvent which is inert in reaction.

5. A method for synthesis of amino acids, comprising the steps of:
hydrating acetylene-carboxylic acids in the presence of a metal salt whose central metal element is Ru and which is represented by General Formula (1); and
adding a transition metal complex whose central metal element is Ru and which is represented by General Formula (3) and a hydrogen and nitrogen atom donor to a reaction system of the hydrated acetylene-carboxylic acids so as to cause a reaction thereof, General Formula (1)

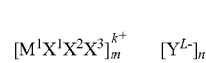

where $M^1$ represents Ru, Rh or Ir, and $X^1$ and $X^2$ ligand represents halogen, $H_2O$, or a solvent molecule, and k represents a valence of a cation species, and Y represents an anion species, and L represents a valence of the anion species, and each of K and L independently represents 1 or 2, and k×m=L×n, General Formula (3)

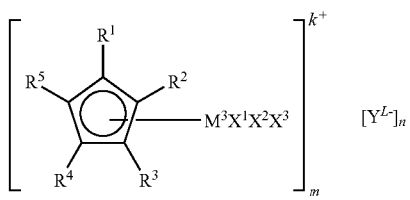

where each of $R^1$, $R^2$, $R^3$, $R^4$, and $R^5$ independently represents a hydrogen atom or a $C_1$ to $C_6$ lower alkyl group, and $M^3$ represents Ru, Rh or Ir, and each of $X^1$ and $X^2$ represents nitrous ligand, and $X^3$ represents a hydrogen atom, a carboxylic acid residue, or $H_2O$, and $X^1$ and $X^2$ may be bonded to each other, and k represents a valence of a cation species, and Y represents an anion species, and L represents a valence of the anion species, and each of K and L independently represents 1 or 2, and k×m=L×n.

6. A method for synthesis of amino acids, comprising the steps of:
  hydrating acetylene-carboxylic acids in the presence of a metal salt whose central metal element is Ru and which is represented by General Formula (1); and
  adding organic ligand respectively represented by General Formula (4) and General Formula (5) and a hydrogen and nitrogen atom donor to a reaction system of the hydrated acetylene-carboxylic acids so as to cause a reaction thereof,

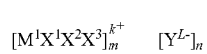

General Formula (1)

where $M^1$ Ru, Rh or Ir, and $X^1$, $X^2$, and $X^3$ ligand represents halogen, $H_2O$, or a solvent molecule, and k represents a valence of a cation species, and Y represents an anion species, and L represents a valence of the anion species, and each of K and L independently represents 1 or 2, and k×m=L×n,

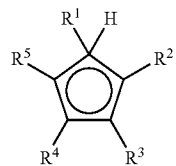

General Formula (4)

where each of $R^1$, $R^2$, $R^3$, $R^4$, and $R^5$ independently represents a hydrogen atom or a $C_1$ to $C_6$ lower alkyl group,

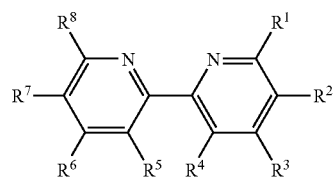

General Formula (5)

where each of $R^1$, $R^2$, $R^3$, $R^4$, $R^5$, $R^6$, $R^7$, and $R^8$ independently represents a hydrogen atom or a $C_1$ to $C_6$ lower alkyl group.

* * * * *